(12) United States Patent
Kim et al.

(10) Patent No.: US 10,644,194 B2
(45) Date of Patent: May 5, 2020

(54) LIGHT-EMITTING DEVICE, LIGHT-EMITTING DEVICE PACKAGE, AND LIGHT-EMITTING MODULE

(71) Applicant: LG INNOTEK CO., LTD., Seoul (KR)

(72) Inventors: Myung Hee Kim, Seoul (KR); Jung Yeop Hong, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 0 days.

(21) Appl. No.: 16/093,795

(22) PCT Filed: Apr. 14, 2017

(86) PCT No.: PCT/KR2017/004065
§ 371 (c)(1),
(2) Date: Oct. 15, 2018

(87) PCT Pub. No.: WO2017/179944
PCT Pub. Date: Oct. 19, 2017

(65) Prior Publication Data
US 2019/0140137 A1 May 9, 2019

(30) Foreign Application Priority Data

Apr. 15, 2016 (KR) .................. 10-2016-0046356
Apr. 22, 2016 (KR) .................. 10-2016-0049327

(51) Int. Cl.
*H01L 33/06* (2010.01)
*H01L 33/32* (2010.01)
(Continued)

(52) U.S. Cl.
CPC .............. *H01L 33/06* (2013.01); *A61N 5/06* (2013.01); *H01L 33/04* (2013.01); *H01L 33/32* (2013.01);
(Continued)

(58) Field of Classification Search
CPC ......... H01L 33/06; H01L 33/32; H01L 33/38; H01L 25/0753
See application file for complete search history.

(56) References Cited

U.S. PATENT DOCUMENTS

2001/0035531 A1 11/2001 Kano et al.
2011/0001127 A1 1/2011 Sakamoto et al.
(Continued)

FOREIGN PATENT DOCUMENTS

EP 1 786 044 5/2007
JP 2001-274096 10/2001
(Continued)

OTHER PUBLICATIONS

International Search Report (with English Translation) and Written Opinion dated Jul. 31, 2017 issued in Application No. PCT/KR2017/004065.

(Continued)

*Primary Examiner* — Christine A Enad
(74) *Attorney, Agent, or Firm* — KED & Associates, LLP

(57) ABSTRACT

Disclosed in an embodiment are a light emitting device, and a light emitting device package and a light emitting module having the same. According to an embodiment, the light emitting device comprises: a first superlattice layer arranged on an AlN template layer, and a first semiconductor layer, a second superlattice layer, and a first conductive semiconductor layer; an active layer having a quantum well layer and a quantum wall layer arranged on the first conductive semiconductor layer; and an electron blocking layer arranged on the active layer and a second conductive semiconductor layer. A first and second layers of the first superlattice layer, the first semiconductor layer, and third and fourth layers of the second superlattice layer include AlGaN-based semiconductors, and an aluminum composition of the third layer is higher than an aluminum composition of the
(Continued)

fourth layer and has the same composition range as that of an aluminum composition of the first semiconductor layer. The active layer emits ultraviolet light.

4 Claims, 17 Drawing Sheets

(51) Int. Cl.
*A61N 5/06* (2006.01)
*H01L 33/04* (2010.01)
*H01L 25/075* (2006.01)
*H01L 33/64* (2010.01)
*H01L 25/16* (2006.01)
*H01L 33/38* (2010.01)

(52) U.S. Cl.
CPC ........ *H01L 25/0753* (2013.01); *H01L 25/167* (2013.01); *H01L 33/38* (2013.01); *H01L 33/64* (2013.01)

(56) References Cited

U.S. PATENT DOCUMENTS

| | | |
|---|---|---|
| 2013/0256630 A1 | 10/2013 | Han et al. |
| 2014/0042454 A1 | 2/2014 | Lee et al. |
| 2014/0103289 A1 | 4/2014 | Liao et al. |
| 2014/0209862 A1 | 7/2014 | Ikuta et al. |
| 2015/0060908 A1* | 3/2015 | Jain .................. H01L 31/03527 257/94 |
| 2015/0083994 A1 | 3/2015 | Jain et al. |

FOREIGN PATENT DOCUMENTS

| | | |
|---|---|---|
| JP | 2013-021124 | 1/2013 |
| KR | 10-2015-0015760 | 2/2015 |
| KR | 10-2016-0001951 | 1/2016 |
| KR | 10-2016-0014416 | 2/2016 |

OTHER PUBLICATIONS

Kawasaki Koji et al.: "Vertical AlGaN deep ultraviolet light emitting diode emitting at 322 nm fabricated by the laser lift-off technique", Applied Physics Letters, AIP Publishing LLC, US, vol. 89, No. 26, Dec. 28, 2006, pp. 261114-261114-3, XP012087834.
European Search Report dated Mar. 1, 2019 issued in Application No. 17782699.7.

* cited by examiner

LIGHT-EMITTING DEVICE, LIGHT-EMITTING DEVICE PACKAGE, AND LIGHT-EMITTING MODULE

CROSS-REFERENCE TO RELATED PATENT APPLICATIONS

This application is a U.S. National Stage Application under 35 U.S.C. § 371 of PCT Application No. PCT/KR2017/004065, filed Apr. 14, 2017, which claims priority to Korean Patent Application Nos. 10-2016-0046356, filed Apr. 15, 2016 and 10-2016-0049327 filed Apr. 22, 2016, whose entire disclosures are hereby incorporated by reference.

TECHNICAL FIELD

An embodiment relates to a light emitting device emitting ultraviolet light.

An embodiment relates to a light emitting device package and a light emitting module having a light emitting device emitting ultraviolet light.

An embodiment relates to a medical equipment having an ultraviolet light emitting device.

BACKGROUND ART

A light emitting diode (LED) is one of light emitting devices that emit light when a current is applied. The LED may emit light with high efficiency at low voltage, thereby having an excellent effect in energy saving.

A nitride semiconductor has received a great interest in a development field of an optical device and a high-power electronic device due to high thermal stability and wide band gap energy thereof. In particular, an ultraviolet (UV) LED, a blue LED, a green LED, a red LED, and the like using the nitride semiconductor are commercialized and used widely.

The ultraviolet light emitting device (UV LED) is a light emitting device that emits light in a wavelength range of 200 to 400 nm. The UV LED is composed of a short wavelength and a long wavelength depending on an application. The short wavelength is used for sterilization or purification, and the long wavelength may be used in an exposure apparatus or a curing apparatus, etc. Particularly, a UVB of a wavelength range of 280 to 315 nm may be used for a medical, etc.

Recently, a UV LED of a UVB, which is used for a precision medical equipment and the like, is required to implement a target wavelength within 280 nm to 315 nm and a high efficiency UV LED capable of high current drive. Further, a light emitting module for a medical equipment is required to have a UV LED capable of reducing the number of light emitting devices, implementing uniformity of light of 70% or more and implementing a therapeutic wavelength band.

DISCLOSURE

Technical Problem

An embodiment may provide an ultraviolet light emitting device capable of implementing high current drive, for example, a high current drive of several hundred mA or more.

An embodiment may provide an ultraviolet light emitting device capable of implementing high current and UVB light.

An embodiment may provide an ultraviolet light emitting device capable of improving defects.

An embodiment may provide an ultraviolet light emitting device capable of improving luminous efficiency.

An embodiment may provide an ultraviolet light emitting device capable of improving power of light.

An embodiment may provide an ultraviolet light emitting device having a full width at half maximum (FWHM) of 17 nm or less and emitting a UVB of 295 nm to 315 nm, and a light emitting device package having the same. An embodiment may provide an ultraviolet light emitting device capable of improving reliability and a method of manufacturing the same.

An embodiment may provide a light emitting device package and a lighting apparatus having an ultraviolet light emitting device.

An embodiment may provide a light emitting module and a medical equipment capable of improving uniformity of light in a target region.

An embodiment may provide a light emitting module and a medical equipment capable of improving the reliability of an ultraviolet wavelength for therapeutic treatment having a full width at half maximum (FWHM) of 17 nm or less.

An embodiment may provide a light emitting module and a medical equipment that implement a UVB of 300 to 320 nm driven by a high current drive of 200 mA or more, have a full width at half maximum (FWHM) of 17 nm or less, and have uniformity of light of 70% or more.

Technical Solution

A light emitting device according to an embodiment comprises: an AlN template layer; a first superlattice layer disposed on the AlN template layer; a second superlattice layer disposed on the first superlattice layer; a first semiconductor layer disposed between the first and second superlattice layers; a first conductive type semiconductor layer disposed on the first second superlattice layer; an active layer disposed on the first conductive type semiconductor layer and having a quantum well layer and a quantum wall layer; an electron blocking layer disposed on the active layer; and a second conductive type semiconductor layer disposed on the electron blocking layer, wherein the first superlattice layer includes a first layer having an AlN semiconductor and a second layer having an AlGaN-based semiconductor, the first semiconductor layer includes an AlGaN-based semiconductor, the second superlattice layer includes a third layer having an AlGaN-based semiconductor and a fourth layer having an AlGaN-based semiconductor, the first layer and the second layer are disposed alternately in the first superlattice layer, the third layer and the fourth layer are disposed alternately in the second superlattice layer, a composition of aluminum (Al) in compound composition formula of the first semiconductor layer, the second layer and the third layer is equal to or greater than a composition of gallium (Ga), and a difference between the composition of gallium and the composition of aluminum is 10% or less, the first semiconductor layer has a thickness greater than that of a single pair having the first layer and the second layer of the first superlattice layer, and the active layer emits ultraviolet light.

An ultraviolet light emitting device according to an embodiment includes: a substrate; an AlN template disposed on the substrate; a first superlattice layer disposed on the AlN template; a second superlattice layer disposed on the first superlattice layer; and a first conductive type first semiconductor layer disposed between the first and second superlattice layers, wherein the first conductive type first semiconductor layer includes an Al composition overlapping with the first and second superlattice layers, thereby improving defects, improving luminous efficiency, power of light, and reliability, and implementing a high current driven UVB of 295 to 315 nm.

According to an embodiment, the composition of aluminum of the first semiconductor layer, the first layer and the third layer may be 50% or more.

According to an embodiment, the first semiconductor layer, the first layer and the third layer may have a composition formula of $Al_xGa_{1-x}N$ ($0.5 \leq x \leq 0.6$), and the fourth layer may have a composition formula of $Al_bGa_{1-b}N$ ($0.45 \leq b \leq 0.55$).

According to an embodiment, the first conductive type semiconductor layer may have a composition formula of $Al_zGa_{1-z}N$ ($0.45 \leq z \leq 0.55$), the quantum well layer of the active layer may be formed of an AlGaN-based semiconductor and the quantum wall layer may be formed of an AlGaN-based semiconductor, and the aluminum composition of the quantum wall layer may be higher than that of the quantum well layer by 20% or more.

According to an embodiment, the quantum well layer has a thickness of 25% or less of a thickness of the quantum wall layer, and the active layer generates light of 295 nm to 315 nm.

According to an embodiment, the electron blocking layer may include a plurality of barrier layers and the plurality of well layers, the plurality of barrier layers may include an AlGaN-based semiconductor, the plurality of well layers may include an AlGaN-based semiconductor, each of the plurality of barrier layers may have an aluminum composition higher than that of each of the plurality of well layers, each of the plurality of barrier layers may have an aluminum composition higher than that of the quantum wall layer of the active layer, each of the plurality of well layers may have an aluminum composition lower than that of the quantum wall layer of the active layer, and the plurality of barrier layers may include a first barrier layer on the active layer and a second barrier layer under the second type conductive semiconductor layer.

According to an embodiment, the plurality of well layers may be disposed between the first and second barrier layers, the plurality of barrier layers may include a plurality of intermediate barrier layers disposed between the first and second barrier layers and the well layer, and an aluminum composition of each of the intermediate barrier layers may be higher than that of the first and second barrier layers.

According to an embodiment, the first barrier layer may have a composition formula of $Al_pGa_{1-p}N$ ($0.50 \leq p \leq 0.74$), the second barrier layer may have a composition formula of $Al_qGa_{1-q}N$ ($0.50 \leq q \leq 0.74$), and the intermediate barrier layer may have a composition formula of $Al_rGa_{1-r}N$ ($0.55 \leq r \leq 0.74$).

According to an embodiment, each of the first barrier layer, the second barrier layer, and the intermediate barrier layer may be thicker than the well layer, and may have a thickness of 3 nm to 10 nm, and a surface roughness of the second conductive type semiconductor layer may be 1 nm or less.

According to an embodiment, the plurality of well layers may include a first well layer disposed between the first barrier layer and the intermediate barrier layer, a second well layer disposed between the intermediate barrier layers and a third well layer between the intermediate barrier layer and the second barrier layer, the first well layer may have a composition formula of $Al_eGa_{1-e}N$ ($0.24 \leq e \leq 0.45$), the second well layer may have a composition formula of $Al_fGa_{1-f}N$ ($0.24 \leq f \leq 0.48$), the third well layer may have a composition formula of $Al_gGa_{1-g}N$ ($0.24 \leq g \leq 0.48$), the second conductive type semiconductor layer may include a first conductive semiconductor layer on the electron blocking layer and a second conductive semiconductor layer on the first conductive semiconductor layer, and the first conductive semiconductor layer may have a composition formula of $Al_sGa_{1-s}N$ ($0.20 \leq s \leq 0.45$).

A light emitting device package according to an embodiment may include: a package body; a heat dissipation frame coupled to the package body; and an ultraviolet light emitting device including any one of 1st through 19th mounted on the heat dissipation frame.

A light emitting module according to an embodiment includes: a circuit board; a light emitting unit including a plurality of light emitting device packages disposed on the circuit board and having a full width at half maximum (FWHM) of 17 nm or less; and a heat dissipation part disposed on a rear surface of the light emitting unit, wherein the plurality of light emitting device packages may have a first pitch in a first direction and a second pitch in a second direction orthogonal to the first direction, and the first pitch and the second pitch may be 30% to 50% of a width or a diameter of a target region irradiated with light from the light emitting unit. Therefore, an embodiment may implement a highly reliable light emitting module for medical treatment with a high efficiency UVB wavelength. Further, an embodiment may implement a target region uniformity of 70% or more and may reduce the number of light emitting device packages, thereby reducing a size and a manufacturing cost of the light emitting module.

A medical equipment according to an embodiment may implement a highly efficient and reliable effective wavelength (300 nm to 320 nm) by including the light emitting module and an optical compensator, and may implement uniformity of a target region of 70% or more and may reduce the number of light emitting device packages, thereby reducing a size and a manufacturing cost of the medical equipment.

A method of manufacturing an ultraviolet light emitting device according to an embodiment includes: forming a first conductive semiconductor layer on a substrate; forming an active layer on the first conductive type semiconductor layer; forming an electron blocking layer (EBL) on the active layer; and forming a second conductive type semiconductor layer on the EBL, wherein the forming of the first conductive type semiconductor layer includes: forming an AlN template on the substrate; forming a first superlattice layer on the AlN template; forming a first conductive type first semiconductor layer on the first superlattice layer; and forming a second superlattice layer on the first superlattice layer, wherein the first conductive type first semiconductor layer may include an Al composition overlapped with the first and second superlattice layers.

Advantageous Effects

An embodiment implements a UV LED having a full width at half maximum (FWHM) of 17 nm or less, and thus the reliability of the UV LED applied to a medical equipment can be improved.

An embodiment can implement a UVB of 295 nm to 315 nm with a high current drive of 100 mA or more by improving carrier injection efficiency by an EBL disposed on an active layer.

An embodiment can improve defects and improve luminous efficiency by disposing a first semiconductor layer, a first superlattice layer, a first conductive type semiconductor layer, and a second superlattice layer between a substrate and an active layer.

An embodiment can improve power of light by an active layer including a quantum well layer having a thickness of 10% to 25% of a thickness of the quantum wall layer.

An embodiment can improve reliability by a second conductive type first semiconductor layer having a thickness of 40 nm or more.

An embodiment can improve power of light and improve light efficiency.

An embodiment can improve the reliability of a light emitting module for light treatment by implementing a light emitting module having a light uniformity of an ultraviolet wavelength irradiated in a target area TA of 70% or more.

An embodiment can improve the reliability of a light emitting module by implementing a light emitting module having a high current drive of 200 mA or more and an ultraviolet wavelength of an effective wavelength (e.g., 300 nm to 320 nm).

An embodiment can provide a light emitting module and a medical equipment capable of improving the reliability of a medical or therapeutic ultraviolet wavelength having a full width at half maximum (FWHM) of 17 nm or less.

In the embodiment, it is possible to reduce the number of light emitting device packages and to reduce the size of a light emitting module by reducing a pitch between the light emitting device packages having the ultraviolet light emitting device.

MODES OF THE INVENTION

In the description of embodiments, it will be understood that when a layer (or film), region, pattern or structure is referred to as being "on/over" or "under" another substrate, layer (or film), region, pattern or structure, the terminologies of "on/over" and "under" include both the meanings of "directly" and "by interposing another layer (indirectly)". Further, the reference with respect to on/over" or "under" each layer will be made on the basis of drawings.

Figure 1:
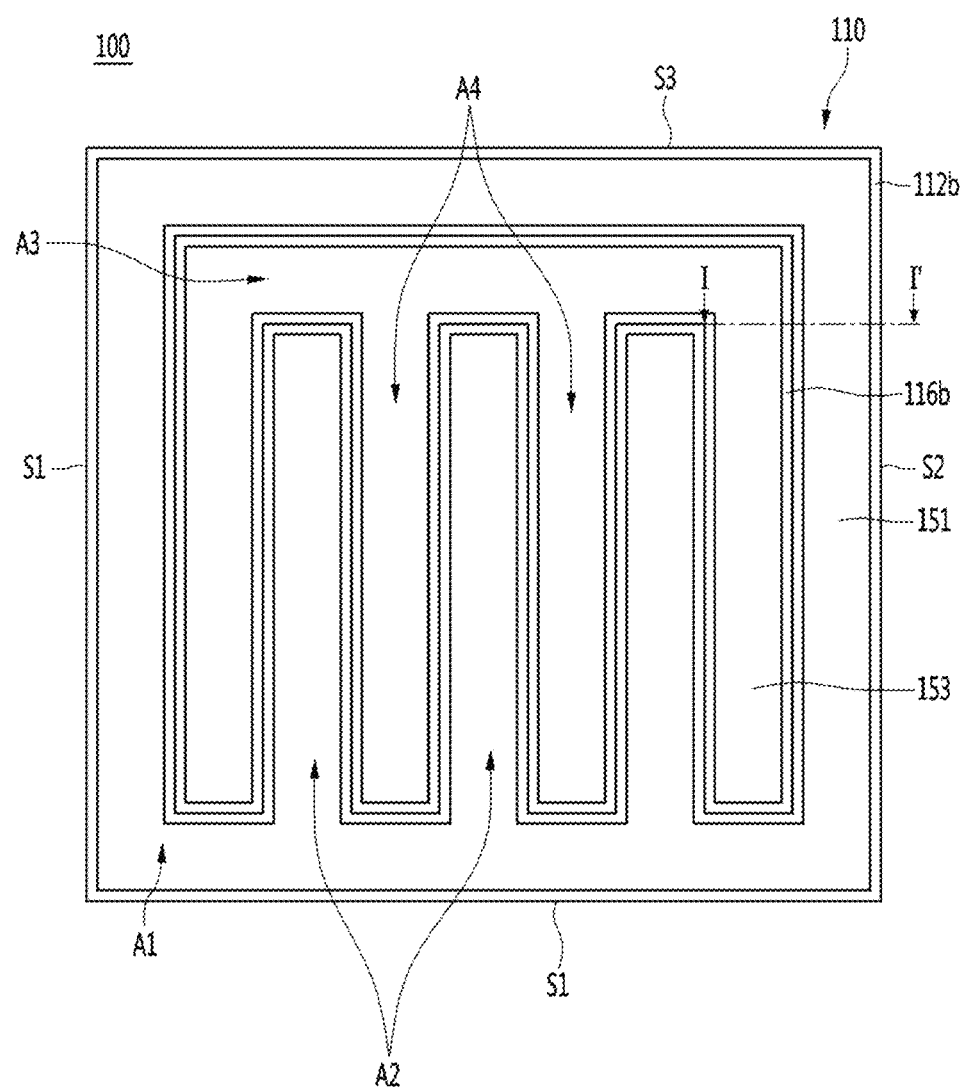
FIG. 1 is a plan view showing a light emitting device according to an embodiment.
Figure 2:
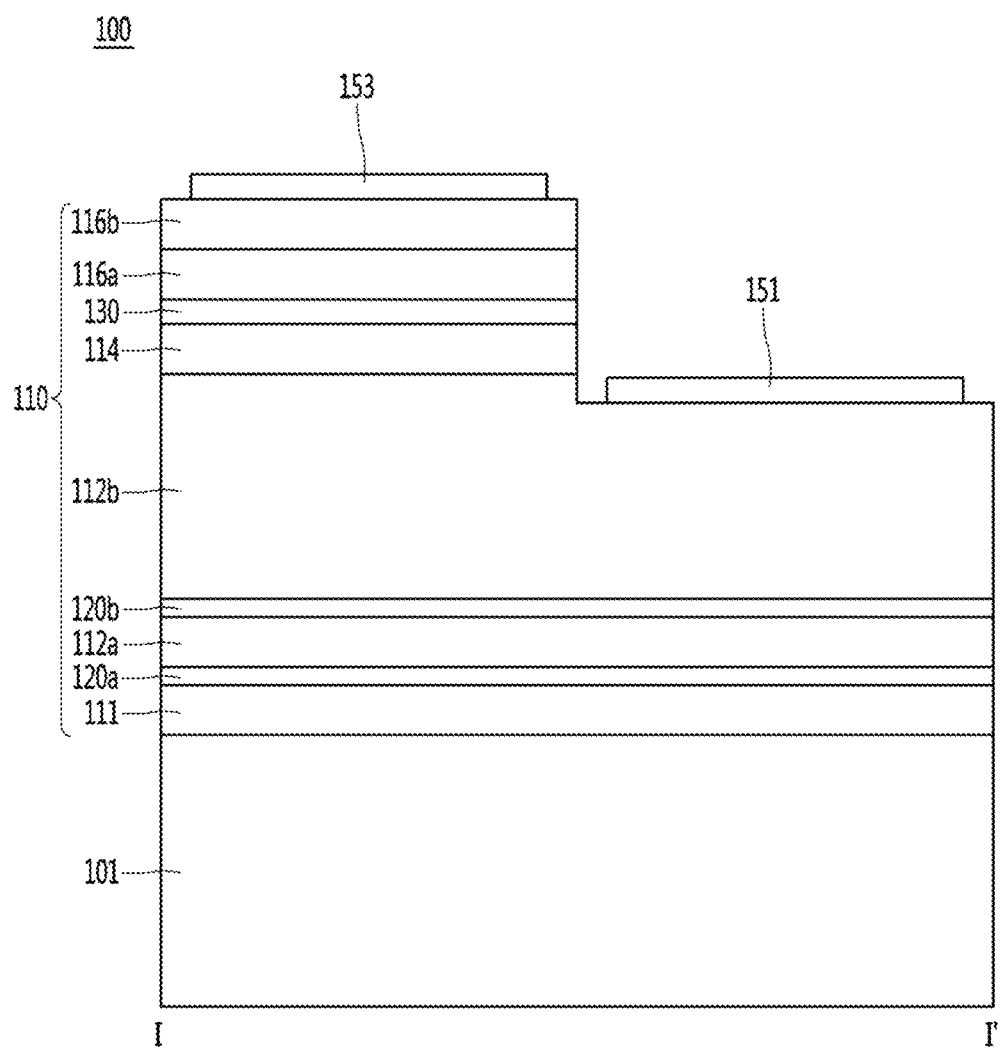
FIG. 2 is a side cross-sectional view of the light emitting device taken along a line I-I' of FIG. 1.
Figure 3:
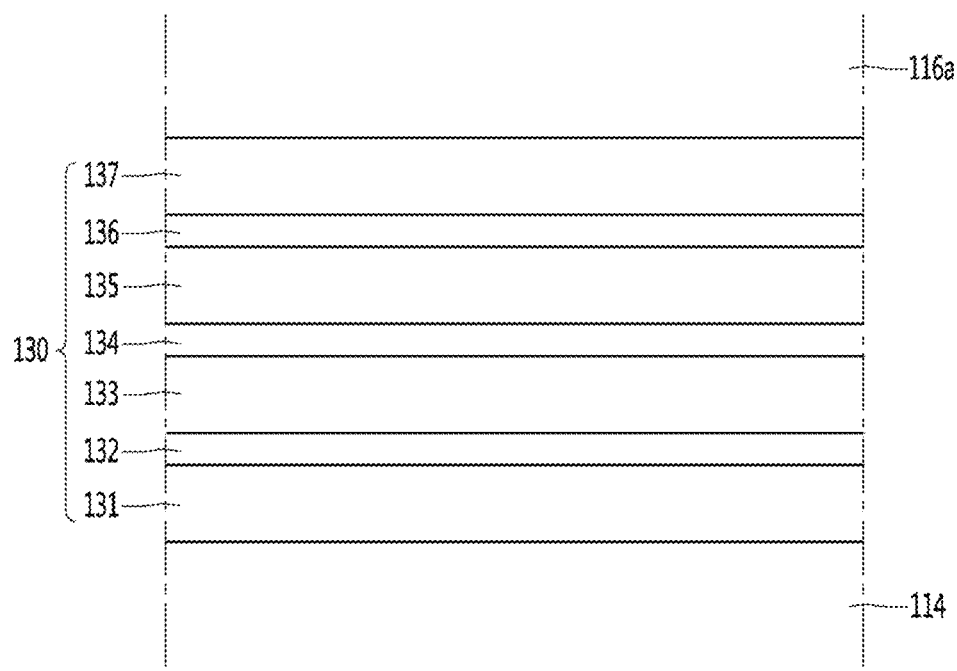
FIG. 3 is a cross-sectional view showing an electron blocking layer between an active layer and a second conductive type semiconductor layer of FIG. 2.
Figure 4:
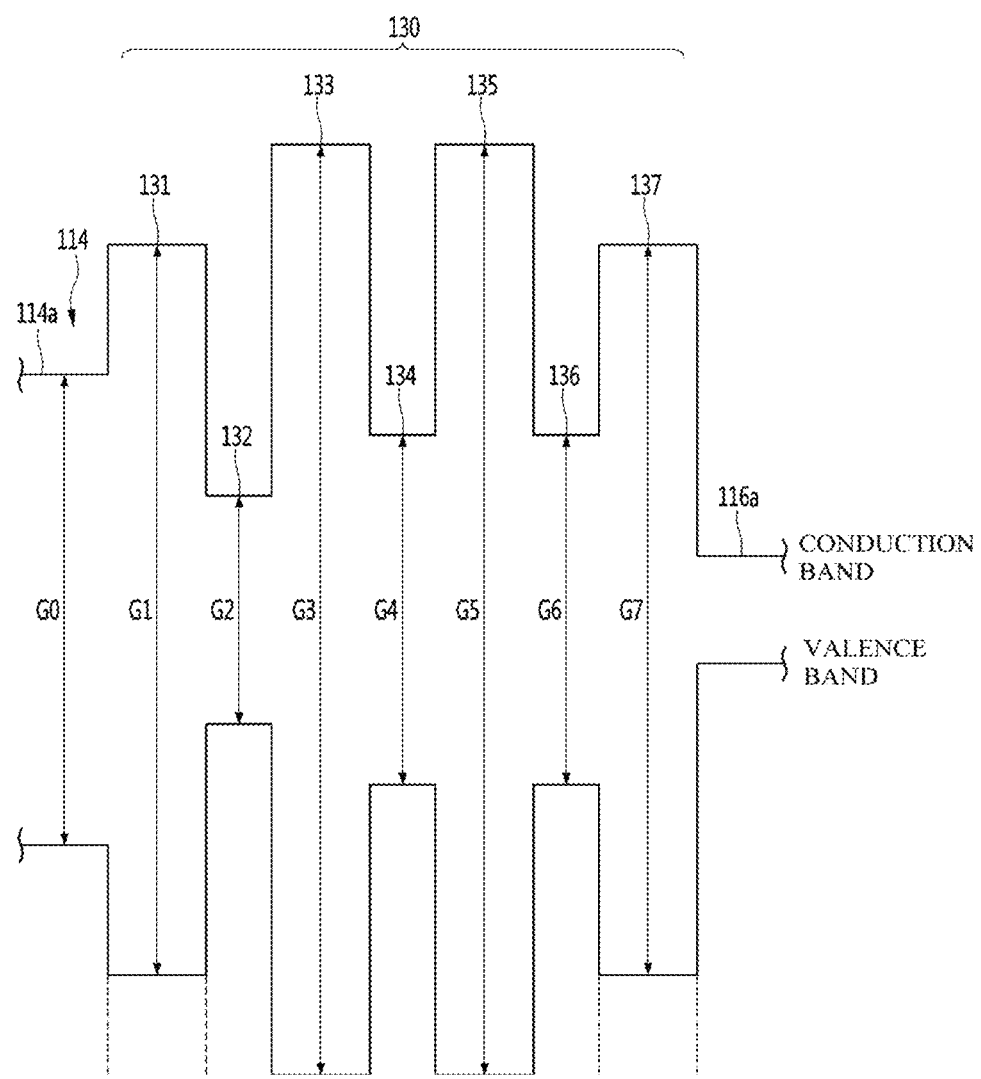
FIG. 4 is a view showing an energy band gap diagram of an electron blocking layer according to an embodiment.
Figure 5:
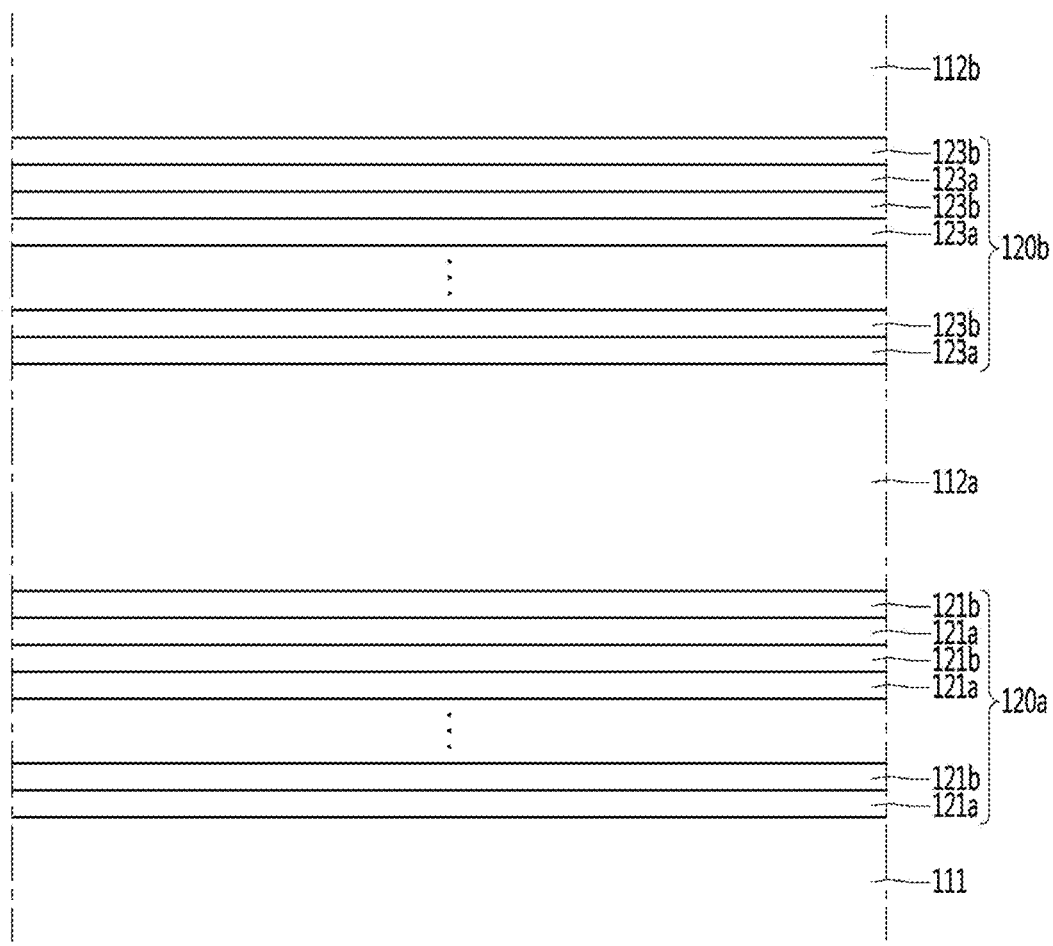
FIG. 5 is cross-sectional view showing an AlN template layer, a first superlattice layer, a first semiconductor layer, a second superlattice layer and a first conductive type semiconductor layer of FIG. 2.

FIG. 1 is a plan view showing a light emitting device according to an embodiment, FIG. 2 is a cross-sectional view of the light emitting device taken along a line I-I' of FIG. 1, FIG. 3 is a detailed view showing an electron blocking layer between an active layer and a second conductive type semiconductor layer of FIG. 2, FIG. 4 is a diagram showing an energy band gap diagram of an electron blocking layer according to an embodiment, and FIG. 5 is a cross-sectional view showing an AlN template layer, a first superlattice layer, a first semiconductor layer, a second superlattice layer, and a first conductive type semiconductor layer of FIG. 2.

As shown in FIGS. 1 to 5, a light emitting device 100 according to an embodiment may include a light emitting structure 110. The light emitting device 100 according to an embodiment may include a substrate 101 and the light emitting structure 110 on the substrate 101. The light emitting device 100 of an embodiment may withstand a high current of 100 mA or more. The light emitting device 100 according to an embodiment includes the light emitting structure 110 that generates light by a high current of 100 mA or more. The light emitting structure 110 may be driven with a high current of 100 mA or more and emit a UVB wavelength. The light emitting device 100 of an embodiment may emit a UVB wavelength of 295 to 315 nm. The light emitting structure 110 of an embodiment may improve defects, improve light emitting efficiency, improve power of light, and improve reliability. The light emitting device 100 according to an embodiment may include an ultraviolet light emitting device emitting UVB light.

As shown in FIG. 1, a top view shape of the light emitting device 100 may be a polygonal shape, for example, a rectangular shape. As another example, the top view shape of the light emitting device 100 may have a circular shape or a square or more shape. A first electrode 151 and a second electrode 153 may be disposed on the light emitting structure 110. The first electrode 151 and the second electrode 153 may be disposed at different heights as shown in FIG. 2, but the present invention is not limited thereto. When the light emitting device 100 is polygonal, the light emitting device 100 may include a plurality of side surfaces S1, S2, S3, and S4.

Regions A1 and A2 in which the first electrode 151 is disposed are regions in which a part of a first conductive type semiconductor layer 112b is exposed, and may be disposed outside regions A3 and A4 in which the second electrode 153 is disposed. For example, a first region A1 in which a part of the first electrode 151 is disposed is disposed at a periphery of a third region A3 in which a part of the second electrode 153 is disposed. One or a plurality of second regions A2 may extend in a direction of a third side surface S3 from the first region A1 and one or a plurality of fourth regions A4 may extend in a direction of a fourth side surface S4 opposite to the third side surface S3 from the third region A3. The second region A2 and the fourth region A4 may be disposed alternately. Branch electrodes branched along the second region A2 may be disposed at the first electrode 151. Branch electrodes branched along the fourth region A4 may be disposed at the second electrode 153.

Referring to FIG. 2, a light emitting structure 110 of an embodiment may include an AlN template layer 111, a first superlattice layer 120a, a first semiconductor layer 112a, a second superlattice layer 120b, a first conductive type semiconductor layer 112b, an active layer 114, an electron blocking layer 130, a second conductive type semiconductor layers 116a and 116b, a first electrode 151, and a second electrode 153.

The substrate 101 may be formed of a material having excellent thermal conductivity, and may be a conductive substrate or an insulating substrate. For example, the substrate 101 may use at least one of sapphire ($Al_2O_3$), SiC, Si, GaAs, GaN, ZnO, GaP, InP, Ge, and $Ga_2O_3$. A concave-convex structure may be formed at an upper surface of the substrate 101, but is not limited thereto. The substrate 101 may be removed.

The AlN template layer 111 may be formed on the substrate 101. The AlN template layer 111 may include a buffer function. The AlN template layer 111 may alleviate the lattice mismatch between materials of the light emitting structure 110 formed on the AlN template layer 111 and the substrate 101. The AlN template layer 111 may be formed of at least one of a Group III-V or Group II-VI compound semiconductor such as GaN, InN, InGaN, AlGaN, InAlGaN, and AlInN in addition to AlN. The AlN template layer 111 may improve defects due to a difference in lattice constant of AlGaN-based semiconductor layers grown on the substrate 101. The AlN template layer 111 may have a fully-strain epitaxial structure, thereby improving luminous efficiency in the growth of a semiconductor layer having an ultraviolet wavelength. That is, the AlN template layer 111 may improve luminous efficiency of an ultraviolet light emitting device 100 by improving the crystallinity of the AlGaN-based semiconductor layers to be grown thereafter. The AlN template layer 111 may be removed.

The first superlattice layer 120a may be disposed on the AlN template layer 111. The first semiconductor layer 112a may be disposed on the first superlattice layer 120a. The second superlattice layer 120b may be disposed on the first semiconductor layer 112a. The first conductive type semiconductor layer 112b may be disposed on the second superlattice layer 120b. The first superlattice layer 120a, the first semiconductor layer 112a, the second superlattice layer 120b, and the first conductive type semiconductor layer 112b may have a composition of aluminum (Al). Any one layer of the first superlattice layer 120a, the first semiconductor layer 112a, the second superlattice layer 120b, and the first conductive type semiconductor layer 112b may include AlGaN or an AlGaN-based semiconductor.

A composition of aluminum (Al) may be gradually lowered as the first superlattice layer 120a, the first semiconductor layer 112a, the second superlattice layer 120b, and the first conductive type semiconductor layer 112b are adjacent to the active layer 114. Accordingly, lattice mismatch and defects between the AlN template layer 111 and the active layer 114 may be improved.

The first superlattice layer 120a may be formed on the AlN template layer 111. The first superlattice layer 120a is disposed on the AlN template layer 111, so that the lattice mismatch and defects between materials of the AlN template layer 111 and the light emitting structure 110 formed on the first superlattice layer 120a may be improved. The first superlattice layer 120a may have an Al composition that is closer to the aluminum composition of the first semiconductor layer 112a than the aluminum composition of the AlN template layer 111. Such a first superlattice layer 120a may improve defects between layers grown on the AlN template layer 111.

As shown in FIGS. 2 and 5, the first superlattice layer 120a may be disposed in two pairs or more, with at least two layers forming one pair. The first superlattice layer 120a may include, for example, a first layer 121a and a second layer 121b. Pairs of the first and second layers 121a and 121b may include 10 to 20 pairs, and may be alternately disposed. The first layer 121a may include an AlN semiconductor, and the second layer 121b may include AlGaN or an AlGaN-based semiconductor. The first layer 121a of the first layer 121a and the second layer 121b may be disposed more adjacent to or in contact with the AlN template layer 111. The second layer 121b may include a semiconductor material having a composition formula of $Al_xGa_{1-x}N$ ($0.5 \leq x \leq 0.6$). The first layer 121a may have an aluminum composition of 100% and the second layer 121b may include an aluminum composition of 50 to 60%. The composition of aluminum at the first and second layers 121a and 121b may be a composition excluding a nitride semiconductor. A thickness of each of the first layer 121a and the second layer 121b of an embodiment may be 5 nm or less, for example, 1 to 5 nm. When the first layer 121a and the second layer 121b are one pair, the number of two layers may be the same, or one of the two layers may be more.

When the first layer 121a and the second layer 121b are less than 10 pairs in the first superlattice layer 120a, a defect improvement effect may be lowered. When the first layer 121a and the second layer 121b are more than 20 pairs in the first superlattice layer 120a, crystallinity may be lowered due to the difference in lattice constant. The second layer 121b may be AlGaN having a first conductive type dopant. The second layer 121b may be an unintentionally doped (hereinafter abbreviated as UID) nitride semiconductor. For example, the second layer 121b may be AlGaN unintentionally having a first conductive type during a growth process. The first and second layers 121a and 121b may have a concentration lower than that of a first conductive type dopant added to the first conductive type semiconductor layer 112b. Any one or both of the first and second layers 121a and 121b may be a UID layer.

The first semiconductor layer 112a may be formed on the first superlattice layer 120a. The first semiconductor layer 112a may be implemented as a compound semiconductor such as a Group III-V or Group II-VI. The first semiconductor layer 112a may be formed of any one or more of GaN, InN, AlN, InGaN, AlGaN, InAlGaN, AlInN, AlGaAs, InGaAs, AlInGaAs, GaP, AlGaP, InGaP, AlInGaP and InP. The first semiconductor layer 112a may be disposed between the first superlattice layer 120a and the second superlattice layer 120b. The first semiconductor layer 112a may be in contact with the first superlattice layer 120a and the second superlattice layer 120b. The first semiconductor layer 112a may be a different semiconductor from the first layer 121a of the first superlattice layer 120a. The first semiconductor layer 112a may be the same semiconductor as the second layer 121b of the first superlattice layer 120a.

The first semiconductor layer 112a may include a semiconductor having an aluminum composition. An aluminum composition of the first semiconductor layer 112a may be the same as an aluminum composition range of the second layer 121b of the first superlattice layer 120a. The first semiconductor layer 112a has the same range as the Al composition range of the second layer 121b of the first superlattice layer 120a, so that defects from the first superlattice layer 120a may be absorbed and removed. The first semiconductor layer 112a may include a function of improving lattice mismatch and defects between the first superlattice layer 120a and the second superlattice layer 120b. The aluminum composition of the first semiconductor layer 112a may be 50% or more, or may be 60% or less.

The first semiconductor layer 112a of an embodiment may include a semiconductor material having a composition formula of $Al_yGa_{1-y}N$ (0.5≤y≤0.6). The first semiconductor layer 112a of an embodiment may include an Al composition of 50 to 60%. A thickness of the first semiconductor layer 112a in an embodiment may be in a range of 10 to 1000 nm or 100 to 1000 nm. The thickness of the first semiconductor layer 112a may be disposed to be greater than that of a single pair of the first superlattice layer 120a. The thickness of the first semiconductor layer 112a may be disposed to be greater than that of the first superlattice layer 120a. Such a first semiconductor layer 112a may be formed of a non-superlattice structure, which has a thickness greater than those of the first and second superlattice layers 120a and 120b and may serve as a buffer between the first and second superlattice layers 120a and 120b. In an embodiment, the first semiconductor layer 112a having a thickness of 200 nm is described as an example, but is not limited thereto. The first semiconductor layer 112a may be doped with a first conductive type dopant. When the first conductive type dopant is an n-type semiconductor layer, the first conductive type dopant may include Si, Ge, Sn, Se, or Te as an n-type dopant, but is not limited thereto. As another example, the first semiconductor layer 112a may be a UID semiconductor. The first semiconductor layer 112a may be a single layer or multiple layers.

As shown in FIGS. 2 and 5, the second superlattice layer 120b may be formed on the first semiconductor layer 112a. The second superlattice layer 120b may be disposed in two pairs or more, with at least two layers forming one pair. The second superlattice layer 120b may include a third layer 123a and a fourth layer 123b and each of the third layer 123a and the fourth layer 123b may be disposed in plural. The third and fourth layers 123a and 123b may be disposed alternately. Any one or both of the third and fourth layers 123a and 123b may be the same semiconductor, for example, AlGaN as the first semiconductor layer 112a. Any one of the third and fourth layers 123a and 123b may have the same Al composition range as the aluminum composition range of the first semiconductor layer 112a. Here, the same Al composition may include the aluminum composition range of the first semiconductor layer 112a. The other one of the third and fourth layers 123a and 123b may be a semiconductor having a different composition from that of the first semiconductor layer 112a in the aluminum composition. The second superlattice layer 120b may be disposed on the first semiconductor layer 112a to include a function of improving lattice mismatch and defects between materials of the first semiconductor layer 112a and the light emitting structure 110 formed on the second superlattice layer 120b. The second superlattice layer 120b may include a third layer 123a and a fourth layer 123b which are alternately formed in 10 to 20 pairs. When the third layer 123a and the fourth layer 123b are one pair, the number of two layers may be the same, or one of the two layers may be more.

The third layer 123a may include a semiconductor material having a composition formula of $Al_aGa_{1-a}N$ (0.5≤a≤0.6). The third layer 123a may include an Al composition of 50 to 60%, and a thickness of each of the third layers 123a of an embodiment may be 5 nm or less, for example, 1 to 5 nm. Here, the second layer 121b of the first superlattice layer 120a, the first semiconductor layer 112a, and the third layer 123a of the second superlattice layer 120b may have the same Al composition range. The second layer 121b of the first superlattice layer 120a, the first semiconductor layer 112a, and the third layer 123a of the second superlattice layer 120b may have a lower Al composition than that of the first layer 121a, and may have a higher Al composition than that of a quantum wall layer of the active layer 114.

When the third and fourth layers 123a and 123b and the first semiconductor layer 112a have an Al composition ratio $Al_x$ and a Ga composition ratio $Ga_y$ in the composition formula of an AlGaN-based semiconductor, the third and fourth layers 123a and 123b and the first semiconductor layer 112a may have a composition ratio relationship of $Al_x \geq Ga_y$, and the difference in the composition ratio of $Al_x$ and $Ga_y$ may be 10% or less. When the composition ratio of the AlGaN-based semiconductor of the third and fourth layers 123a and 123b and the first semiconductor layer 112a has a composition ratio relationship of $Al_x < Ga_y$, semiconductor crystals may be improved, but light absorption loss may be increased. When the composition difference between $Al_x$ and $Ga_y$ exceeds 10%, it may affect light absorption loss of an ultraviolet wavelength or semiconductor crystals. In an embodiment, the third and fourth layers 123a and 123b and the first semiconductor layer 112a may optimize the composition ratio in the AlGaN-based semiconductor composition formula to improve the semiconductor crystals and reduce the light absorption loss of the ultraviolet wavelength. In addition, defects transmitted from the first superlattice layer 120a may be absorbed and removed due to the Al composition range of the third and fourth layers 123a and 123b and the first semiconductor layer 112a and the difference thereof. A function of improving lattice mismatches and defects at interfaces between the first and second layers 121a and 121b of the first superlattice layer 120a, the third and fourth layers 123a and 123b of the second superlattice layer 120b, and the first semiconductor layer 112a may be included. The crystallinity of the AlGaN-based semiconductor layers may be improved, and thus luminous efficiency of ultraviolet light may be improved. When the active layer 114 emits a UVB wavelength or a wavelength of 295 to 315 nm, the AlGaN-based semiconductors of the third and fourth layers 123a and 123b and the first semiconductor layer 112a may be provided with the above-described difference in the Al composition of 40% or more, and thus the crystallinity at the time of growing the semiconductor layer may be improved.

The fourth layer 123b may include a semiconductor material having a composition formula of $Al_bGa_{1-b}N$ (0.45≤b≤0.55). The fourth layer 123b may include an Al composition of 45 to 55%. A thickness of each of the fourth layers 123b of an embodiment may be 5 nm or less, for example, 1 to 5 nm. A single pair of the second superlattice layers 120b may be smaller than the thickness of the first semiconductor layer 112a. The thickness of the second superlattice layer 120b may be smaller than that of the first semiconductor layer 112a. The fourth layer 123b may have a lower aluminum composition than that of the third layer 123a. The fourth layer 123b may have a lower aluminum composition of 5% or more than that of the third layer 123a. The fourth layer 123b may be doped with a first conductive type dopant. When the first conductive type dopant is an n-type semiconductor layer, the first conductive type dopant may include Si, Ge, Sn, Se, or Te as an n-type dopant, but is not limited thereto. The first semiconductor layer 112a may be a UID nitride semiconductor. Here, when the first conductive type dopant is an n-type semiconductor layer, the first conductive type dopant may include Si, Ge, Sn, Se, or Te as an n-type dopant, but is not limited thereto. In an embodiment, the Al composition gradually decreases from the AlN template layer 111 to the active layer 114, and thus crystallinity may be improved. Any one or both of the third and fourth layers 123a and 123b may be a UID semiconductor.

The first conductive type semiconductor layer 112b may be formed on the second superlattice layer 120b. The first conductive type semiconductor layer 112b may be implemented as a compound semiconductor such as a Group III-V or Group II-VI. For example, the first conductive type semiconductor layer 112b may be formed of any one or more of GaN, InN, InGaN, AlGaN, InAlGaN, AlInN, AlGaAs, InGaAs, AlInGaAs, GaP, AlGaP, InGaP, AlInGaP and InP. The first conductive type semiconductor layer 112b of an embodiment may include a semiconductor material having a composition formula of $Al_zGa_{1-z}N$ ($0.45 \le z \le 0.55$). When the first conductive type semiconductor layer 112b is in contact with the second superlattice layer 120b, the aluminum composition of the first conductive type semiconductor layer 112b may be the same or lower than that of the fourth layer 123b. Accordingly, the first conductive type semiconductor layer 112b may prevent deterioration in crystal quality of the active layer 114 due to a difference in composition of aluminum.

The first conductive type semiconductor layer 112b of an embodiment may include an Al composition of 45 to 55%, and a thickness of the first conductive type semiconductor layer 112b of an embodiment may be 500 to 1000 nm. The thickness of the first conductive type semiconductor layer 112b may be greater than those of the first superlattice layer 120a, the first semiconductor layer 112a, and the second superlattice layer 120b. As shown in FIG. 1, in the first conductive type semiconductor layer 112b, a partial region, for example, the first and second regions A1 and A2 may be disposed to be lower than a position of the active layer 114. In an embodiment, the first conductive type semiconductor layer 112b having a thickness of 1000 nm is described as an example, but is not limited thereto. The first conductive type semiconductor layer 112b may be doped with a first conductive type dopant. The first electrode 151 may be disposed on the first conductive type semiconductor layer 112b as shown in FIG. 2. The first conductive type semiconductor layer 112b may be an electrode contact layer. The first electrode 151 disposed on the first conductive type semiconductor layer 112b is described as an example, but the first electrode 151 may be connected to the first conductive type semiconductor layer 112b with a via structure passing through the substrate 101 or may be connected with a via structure passing through the second conductive type semiconductor layers 116a and 116b. The first electrode 151 may be connected to the second superlattice layer 120b, not the first conductive type semiconductor layer 112b, but is not limited thereto. The active layer 114 may be formed as at least one of a single quantum well structure, a multi-quantum well (MQW) structure, a quantum-wire structure, and a quantum dot structure. The active layer 114 is a layer at which electrons (or holes) injected through the first conductive type semiconductor layer 112b and holes (or electrons) injected through the second conductive type semiconductor layers 116a and 116b meet each other, and emits light by a difference in band gap of an energy band according to a material forming the active layer 114.

The active layer 114 may be composed of a compound semiconductor. The active layer 114 may be implemented with at least one of compound semiconductors such as a Group III-V or Group II-VI as an example. The active layer 114 may include a quantum well layer and a quantum wall layer. The quantum well layer may be disposed in plural, and the quantum wall layer may be disposed in plural. When the active layer 114 is implemented with an MQW structure, the quantum well layer and the quantum wall layer may be alternately disposed. The quantum well layer and the quantum wall layer may be formed in a structure of any one or more pairs of AlGaN/GaN, AlGaN/AlGaN, InGaN/GaN, InGaN/InGaN, InAlGaN/GaN, GaAs/AlGaAs, InGaAs/AlGaAs, GaP/AlGaP, and InGaP/AlGaP, but are not limited thereto.

The active layer 114 may include AlGaN or an AlGaN-based semiconductor to emit an ultraviolet wavelength. In the active layer 114, the quantum well layer may include an AlGaN-based semiconductor, and the quantum wall layer may include an AlGaN-based semiconductor. An aluminum composition of the quantum well layer may be lower than that of the quantum wall layer, and for example, may be 20% or less based on the aluminum composition of the quantum wall layer. The aluminum composition of the quantum well layer may be 30% or less, for example, in a range of 15% to 30%, and the aluminum composition of the quantum wall layer may be in a range of 45 to 52%. The aluminum composition of the quantum wall layer may have a difference from that of the quantum well layer in a range of 20% or more, for example, 20 to 30%. The active layer 114 may emit ultraviolet light by the difference in the aluminum composition ratio of the quantum well layer and the quantum wall layer. The active layer 114 may emit light having a UVB wavelength. The active layer 114 may emit UVB of 295 to 315 nm. The ultraviolet ray B (UVB) has a wavelength shorter than that of ultraviolet ray A (UVA) and the energy intensity of a light beam has characteristics stronger than that of the ultraviolet ray A (UVA). Such ultraviolet ray B may be used as a medical light source. The ultraviolet light emitted from the active layer 114 of an embodiment may have a full width at half maximum (FWHM) of 17 nm or less.

Figure 6:
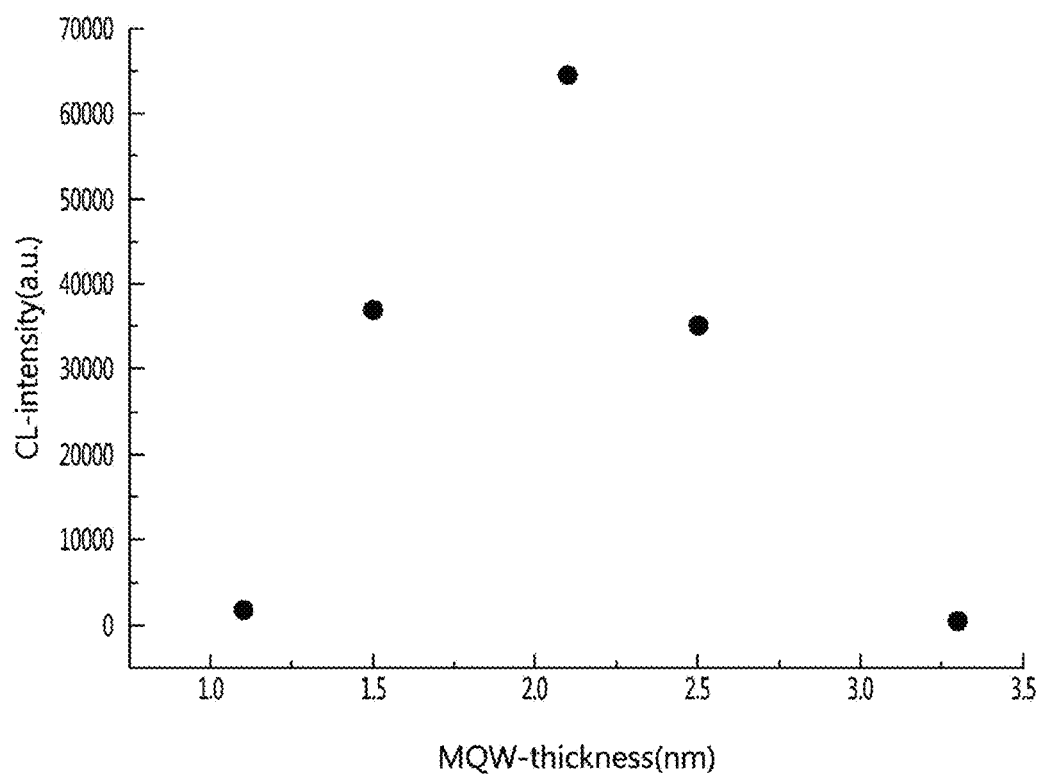
FIG. 6 is a graph showing a power of light according to a thickness of a quantum wall layer of an active layer according to an embodiment.

In the active layer 114, a thickness of the quantum well layer may be thinner than that of the quantum wall layer. The thickness of the quantum well layer may be 25% or less of the quantum wall layer, for example, in a range of 10 to 25%. That is, the thickness of the quantum wall layer may be four times or more, for example, four to ten times the thickness of the quantum well layer. Referring to FIG. 6, the active layer 114 of an embodiment may improve power of light by quantum well layers having a thickness of 10% to 25% of the quantum wall layer. For example, each of the quantum well layers may be 2.5 nm or less, for example, 1.5 nm to 2.5 nm. FIG. 6 is a graph showing the power of light according to the thickness of the quantum well layer of the active layer 114 having the quantum wall layer of 10.9 nm, and shows the highest light power in the quantum well layer having the thickness of 2.1 nm. When the thickness of each of the quantum well layers is less than 10% or more than 25% of the thickness of each of the quantum wall layers, crystallinity may be deteriorated or a carrier movement may be deteriorated. When the thickness of each of the quantum well layers is out of the range of 10% to 25% of the thickness of each of the quantum wall layers, the recombination rate of electrons and holes from the active layer 114 may be lowered and the power of light may be deteriorated.

Referring to FIGS. 3 and 4, the electron blocking layer (EBL) 130 may be formed on the active layer 114. The electron blocking layer 130 may be disposed between the active layer 114 and the second conductive type semiconductor layers 116a and 116b. The EBL 130 may include a multilayer structure, and at least one or all of the multiple layers may include a second conductive type dopant. The electron blocking layer 130 may include AlGaN or an AlGaN-based semiconductor to reduce absorption of an ultraviolet wavelength and to block electrons.

The EBL 130 of an embodiment may include a plurality of barrier layers 131, 133, 135, and 137, and a plurality of well layers 132, 134, and 136. Any one or more of the barrier layers 131, 133, 135, and 137 and the well layers 132, 134, and 136 may be the same, or any one of the layers may be more. The EBL 130 may be formed of a Group III-V or II-VI compound semiconductor, for example, the EBL 130 may be formed of three or more pairs of AlGaN/AlGaN, but is not limited thereto. At least one layer or all of the EBL 130 may be doped with a second conductive type dopant. For example, when the EBL 130 is a p-type semiconductor layer, the second conductive type dopant may include Mg, Zn, Ca, Sr, or Ba as a p-type dopant. The EBL 130 of an embodiment may include a function for increasing a carrier provided to the active layer 114 to implement a UVB of 295 to 315 nm of a high current drive of 100 mA or more. In addition, the EBL 130 may include an electron blocking function for blocking electrons, and thus luminous efficiency may be improved. The EBL 130 may be formed such that a plurality of barrier layers 131, 133, 135, and 137 and a plurality of well layers 132, 134, and 136 are alternated in three or more pairs. The plurality of barrier layers 131, 133, 135, and 137 and the plurality of well layers 132, 134, and 136 may include a second conductive type dopant. The well layers 132, 134 and 136 may be relatively thinner than thicknesses of the barrier layers 131, 133, 135 and 137, so that the second conductive type dopant may not be doped. The plurality of barrier layers 131, 133, 135, and 137 and the plurality of well layers 132, 134, and 136 of an embodiment may improve luminous efficiency by the Al composition and thickness.

The EBL 130 may prevent an overflow of electrons having passed through the active layer 114 to improve internal quantum efficiency. As shown in FIG. 4, the EBL 130 includes barrier layers 131, 133, 135, and 137 having a higher energy level and well layers 132, 134, and 136 having a lower energy level based on an energy level reference (REF) of a quantum wall layer 114a (see FIG. 4) of the active layer 114. The quantum wall layer may be a last layer of the quantum wall layers of the active layer 114. The last quantum wall layer of the active layer 114 may have the same aluminum composition as the other quantum wall layers.

The barrier layers 131, 133, 135 and 137 of the EBL 130 may have a higher aluminum composition than that of the last quantum wall layer 114a (see FIG. 4) of the active layer 114, and the well layers 132, 134, and 136 may have a lower aluminum composition than that of the last quantum wall layer 114a (see FIG. 4) of the active layer 114. The last quantum wall layer 114a (see FIG. 4) of the active layer 114 may include an Al composition of 45% to 52%, and the plurality of barrier layers 131, 133, 135, and 137 may include an Al composition of 50% or more. The last quantum wall layer 114a of the active layer 114 may have a lower aluminum composition than that of the barrier layers 131, 133, 135, and 137. The barrier layers 131, 133, 135, and 137 may have a higher aluminum composition of 3% or more than that of the last quantum wall layer 114a of the active layer 114.

The Al composition of the EBL 130 may block electrons and confine holes to improve luminous efficiency by increasing carrier injection of the active layer 114.

The plurality of barrier layers 131, 133, 135, and 137 may include a first barrier layer 131 adjacent to the active layer 114, a second barrier layer 137 adjacent to the second conductive type semiconductor layers 116a and 116b, and intermediate barrier layers 133 and 135 between the first barrier layer 131 and the second barrier layer 137. Here, the intermediate barrier layers 133 and 135 may be disposed in one or plural. In the case of the plurality of barrier layers 133 and 135, a first intermediate barrier layer 133 between the first barrier layer 131 and the second barrier layer 137, and a second intermediate barrier layer 135 between the first intermediate barrier layer 133 and the second barrier layer 137 may be included.

The first barrier layer 131 may be in contact with the last quantum wall layer 114a of the active layer 114. The second barrier layer 137 may be in contact with lower surfaces of the second conductive type semiconductor layers 116a and 116b.

The plurality of well layers 132, 134, and 136 may include a first well layer 132 between the first barrier layer 131 and the first intermediate barrier layer 133, a second well layer 134 between the first and second intermediate barrier layers 133 and 135, and a third well layer 136 between the second intermediate barrier layer 135 and the second barrier layer 137. The EBL 130 of an embodiment includes a plurality of barrier layers 131, 133, 135, and 137, and a plurality of well layers 132, 134, and 136 of a three-pair structure, but is not limited thereto. The first barrier layer 131 may have a higher Al composition than that of the last quantum wall layer 114a of the active layer 114. For example, the first barrier layer 131 may include a semiconductor material having a composition formula of $Al_pGa_{1-p}N$ (0.50≤p≤0.74). The first barrier layer 131 of an embodiment may include an Al composition of 50 to 74%, and a thickness W1 of the first barrier layer 131 of an embodiment may be greater than a thickness W2 of the first well layer 132. The thickness W1 of the first barrier layer 131 of an embodiment may be 10 nm or less, for example, 3 nm to 10 nm.

The second barrier layer 137 may have a higher Al composition than that of the second conductive type semiconductor layers 116a and 116b. For example, the second barrier layer 137 may include a semiconductor material having a composition formula of $Al_qGa_{1-q}N$ (0.50≤q≤0.74). The second barrier layer 137 of an embodiment may include an Al composition of 50 to 74% and a thickness W7 of the second barrier layer 137 of an embodiment may be greater than a thickness W6 of the third well layer 136. The thickness W7 of the second barrier layer 137 of an embodiment may be 10 nm or less, for example, 3 to 10 nm. The second barrier layer 137 has an Al composition of 50% to 74% and a thickness of 10 nm or less, and thus electrons may be blocked, carrier injection efficiency may be improved, and light absorption loss of an ultraviolet wavelength may be reduced.

The Al compositions of the first and second intermediate barrier layers 133 and 135 may be the same or have a difference of less than 1%, and may be higher than the Al compositions of the first barrier layer 131 and the second barrier layer 137. The EBL 130 having such an Al composition may improve hole injection. For example, the EBL 130 may improve luminous efficiency by confining holes in the first and second intermediate barrier layers 133 and 135 to increase carrier injection of the active layer 114. The first and second intermediate barrier layers 133 and 135 may include a semiconductor material having a composition formula of $Al_rGa_{1-r}N$ (0.55≤r≤0.74). The first and second intermediate barrier layers 133 and 135 of an embodiment may include an Al composition of 55 to 74%. Thicknesses W3 and W5 of the first and second intermediate barrier layers 133 and 135 of an embodiment may be thicker than a thickness W4 of the second well layer 134. The thicknesses W3 and W5 of the first and second intermediate barrier layers 133 and 135 of an embodiment may be 10 nm or less, for example, 3 to 10 nm. For example, when the EBL 130 includes the first barrier layer 131 and the second barrier layer 137 having an Al composition of 54% and the first and second intermediate barrier layers 133 and 135 having a composition of 64%, an output voltage may be improved by 30% or more than that of the ultraviolet light emitting device of a comparative example having a lower composition than the above-described Al composition.

The plurality of well layers 132, 134 and 136 may include a first well layer 132 between the first barrier layer 131 and the first intermediate barrier layer 133, a second well layer 134 between the first and second intermediate barrier layers 133 and 135, and a third well layer 136 between the second intermediate barrier layer 135 and the second barrier layer 137.

The first well layer 132 may include a lower Al composition than that of the last quantum wall layer 114a of the active layer 114. The first well layer 132 may include a semiconductor material having a composition formula of $Al_eGa_{1-e}N$ (0.24≤e≤0.45). The thickness W2 of the first well layer 132 of an embodiment may be thinner than the thickness W1 of the first barrier layer 131 and the thickness W3 of the first intermediate barrier layer 133. The thickness W2 of the first well layer 132 in an embodiment may be 5 nm or less, for example, 1 to 5 nm.

The second well layer 134 may include a lower Al composition than that of the last quantum wall layer 114a of the active layer 114. The second well layer 134 may include a semiconductor material having a composition formula of $Al_fGa_{1-f}N$ (0.24≤f≤0.48). The thickness W4 of the second well layer 13 of an embodiment may be thinner than the thicknesses W3 and W5 of the first and second intermediate barrier layers 133 and 135. The thickness W4 of the second well layer 134 of an embodiment may be 5 nm or less, for example, 1 to 5 nm.

The third well layer 136 may include a lower Al composition than that of the last quantum wall layer 114a of the active layer 114. The third well layer 136 may include a semiconductor material having a composition formula of $Al_gGa_{1-g}N$ (0.24≤g≤0.48). The thickness W6 of the third well layer 136 of an embodiment may be thinner than the thickness W5 of the second intermediate barrier layer 135 and the thickness W7 of the second barrier layer 137. The thickness W6 of the third well layer 136 of an embodiment may be 5 nm or less, for example, 1 to 5 nm. The second and third well layers 134 and 136 may have the same Al composition and thickness, but are not limited thereto. The Al composition of the second and third well layers 134 and 136 may be higher than that of the first well layer 132.

The EBL 130 may prevent electrons from overflowing due to a difference in Al composition or barrier between the plurality of barrier layers 131, 133, 135, and 137 and the well layers 132, 134, and 136, and thus internal quantum efficiency may be improved.

As shown in FIG. 4, energy band gaps G1, G3, G5 and G7 of the plurality of barrier layers 131, 133, 135 and 137 are larger than an energy band gap G0 of the last quantum wall layer 114a of the active layer 114. When the energy band gap of the first barrier layer 131 is G1, the energy band gaps of the first and second intermediate barrier layers 133 and 135 are G3 and G5, and the energy band gap of the second barrier layer 137 is G7, the energy band gaps may have a relationship of G3, G5>G1, G7>G0.

Energy band gaps G2, G4 and G6 of the plurality of well layers 132, 134 and 136 may be smaller than the energy band gap G0 of the last barrier layer 114a of the active layer 114. When the energy band gap of the first well layer 132 is G2, the energy band gap of the second well layer 134 is G4, and the energy band gap of the third well layer 136 is G6, the energy band gaps may have a relationship of G0>G2>G4, G6.

In an embodiment, the EBL 130 may be disposed on the active layer 114 to improve carrier injection efficiency, and thus the luminous efficiency may be improved. An embodiment may implement a UVB of 295 to 315 nm of a high current drive of 100 mA or more.

The second conductive type semiconductor layers 116a and 116b may be disposed on the EBL 130. The second conductive type semiconductor layers 116a and 116b may be formed as a single layer or multiple layers, and in the case of multiple layers, the multiple layers may include a first conductive semiconductor layer 116a and a second conductive semiconductor layer 116b. The first conductive semiconductor layer 116a may be disposed on the EBL 130 and may be disposed between the EBL 130 and the second conductive semiconductor layer 116b. The first and second conductive semiconductor layers 116a and 116b may be a semiconductor having a second conductive type dopant.

The first conductive semiconductor layer 116a may be implemented as a compound semiconductor such as a Group III-V or Group II-VI. For example, the first conductive semiconductor layer 116a may be formed of any one or more of GaN, InN, InGaN, AlGaN, InAlGaN, AlInN, AlGaAs, InGaAs, AlInGaAs, GaP, AlGaP, InGaP, AlInGaP and InP. The first conductive semiconductor layer 116a may include AlGaN or an AlGaN-based semiconductor to reduce the absorption of an ultraviolet wavelength. The first conductive semiconductor layer 116a of an embodiment may include a semiconductor material having a composition formula of $Al_sGa_{1-s}N$ (0.20≤s≤0.45). The first conductive semiconductor layer 116a may include an Al composition of 20 to 45%.

Figure 7:
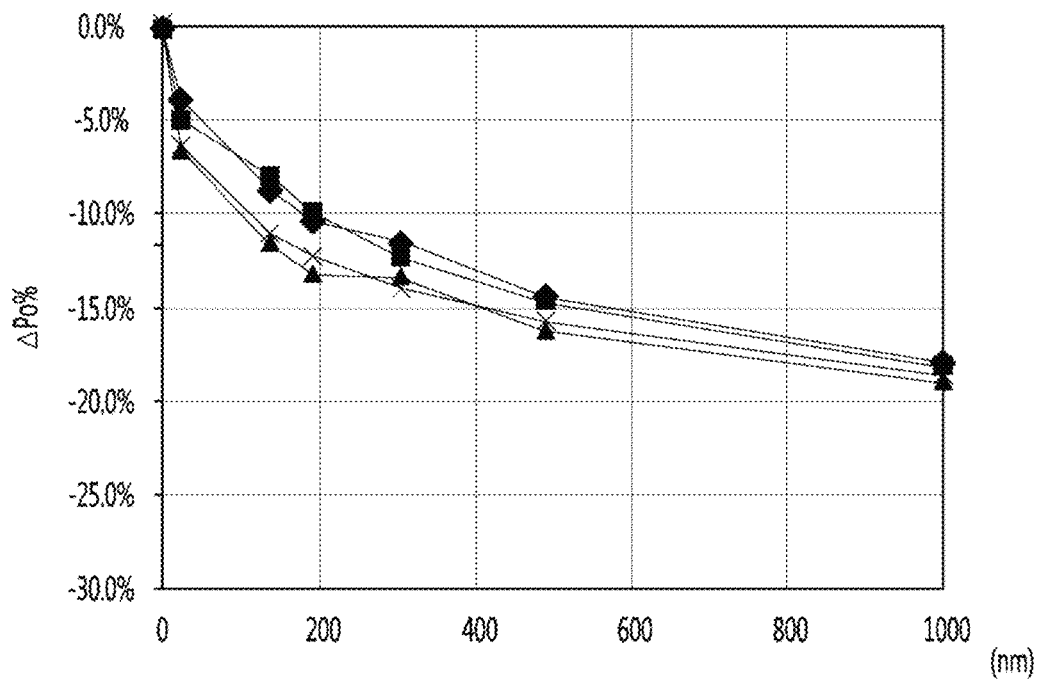
FIG. 7 is a graph showing reliability according to a thickness of a first conductive semiconductor layer of a second conductive type semiconductor layer of an embodiment.

A thickness of the first conductive semiconductor layer 116a may be 40 nm or more. FIG. 7 is a graph showing reliability according to a thickness of a first conductive semiconductor layer of an embodiment. Referring to FIG. 7, when the first conductive semiconductor layer 116a of an embodiment has a thickness of 40 nm or more, a change of an output voltage with time is constant, and thus reliability may be improved. The thickness of the first conductive semiconductor layer 116a of an embodiment may be 40 nm or more, for example, 40 to 300 nm. The first conductive semiconductor layer 116a may be doped with a second conductive type dopant. In the case in which the first conductive semiconductor layer 116a is a p-type semiconductor layer, the second conductive type dopant may include Mg, Zn, Ca, Sr, or Ba as a p-type dopant. When the thickness of the first conductive semiconductor layer 116a of an embodiment is less than 40 nm, reliability may be deteriorated due to an output voltage which gradually decreases according to a driving time of the ultraviolet light emitting device 100.

Here, although the first conductive type semiconductor layer 112b is described as an n-type semiconductor layer and the second conductive type semiconductor layers 116a and 116b are described as p-type semiconductor layers, the first conductive type semiconductor layer 112b may be formed as a p-type semiconductor layer, and the second conductive type semiconductor layers 116a and 116b may be formed as n-type semiconductor layers, but are not limited thereto. A semiconductor, for example, an n-type semiconductor layer (not shown) having a polarity opposite to the polarity of the second conductive type may be formed on the first conductive semiconductor layer 116a and the second conductive semiconductor layer 116b. Accordingly, the light emitting structure 110 may be implemented as any one structure of an n-p junction structure, a p-n junction structure, an n-p-n junction structure, and a p-n-p junction structure.

Figure 8:
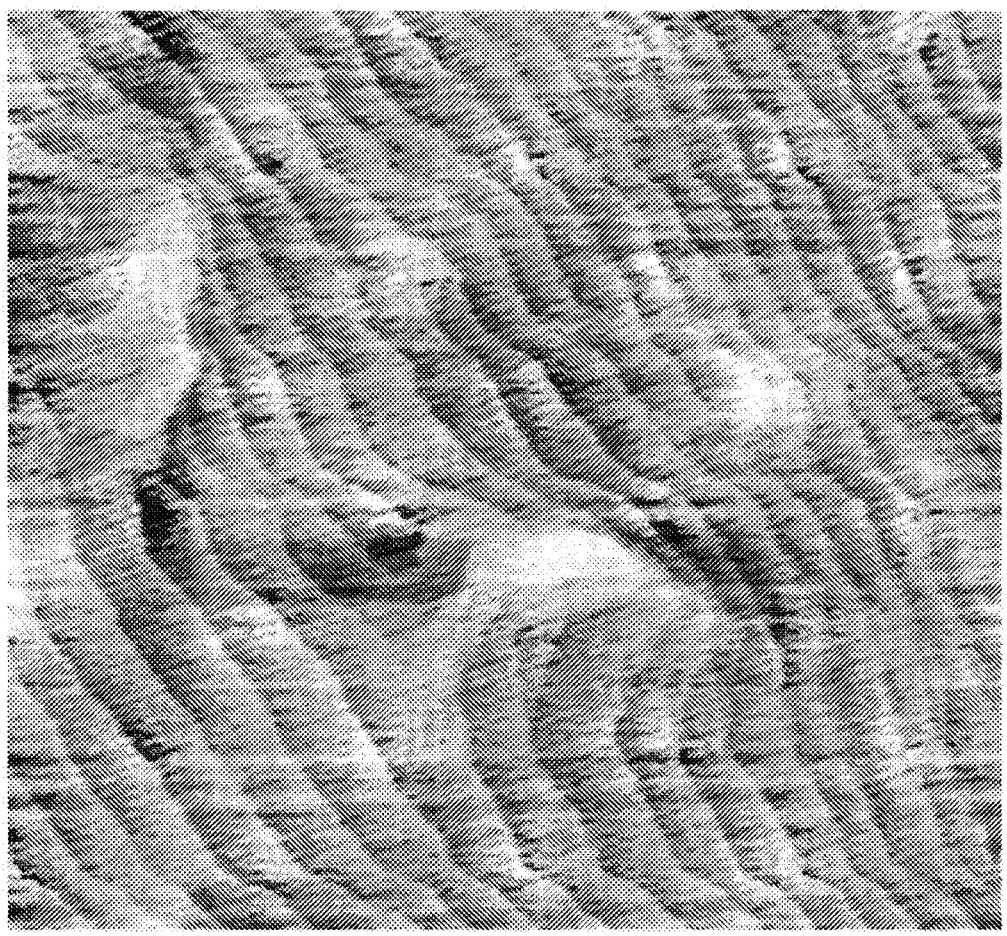
FIG. 8 is a view showing a surface of the second conductive type semiconductor layer of an embodiment.

The second conductive semiconductor layer 116b may be formed on the first conductive semiconductor layer 116a. The second conductive semiconductor layer 116b may be an electrode contact layer which the second electrode 153 contacts. The second conductive semiconductor layer 116b may be formed of a semiconductor different from the first conductive semiconductor layer 116a. For example, the second conductive semiconductor layer 116b may have a lower Al composition than that of the first conductive semiconductor layer 116a, or may be a GaN-based semiconductor having no Al composition. The second conductive semiconductor layer 116b may be disposed between the first conductive semiconductor layer 116a and the second electrode 153 for ohmic contact between the first conductive semiconductor layer 116a and the second electrode 153. The second conductive semiconductor layer 116b may be a GaN including a second conductive type or a second conductive type dopant for ohmic contact between the first conductive semiconductor layer 116a and the second electrode 153, but is not limited thereto. A surface of the second conductive semiconductor layer 116b directly contacting the second electrode 153 may be flat. For this, the second conductive semiconductor layer 116b may be formed by a 2-dimension (D) growth method. A surface of the second conductive semiconductor layer 116b may be formed as a rough surface. FIG. 8 is a view showing a surface of the second conductive semiconductor layer 116b of an embodiment. The second conductive semiconductor layer 116b of an embodiment has a thickness of 50 nm or less for the ohmic contact between the first conductive semiconductor layer 116a and the second electrode 153 and has a surface roughness (RMS) of 1 nm or less, for example, 0.1 to 1.0 nm. The second conductive semiconductor layer 116b of an embodiment may include a surface roughness (RMS) of 1 nm or less to improve reliability of contact with the second electrode 153 formed later.

The first electrode 151 may be disposed on the first conductive type semiconductor layer 112b. The first electrode 151 may be electrically connected to the first conductive type semiconductor layer 112b. The first electrode 151 may be electrically insulated from the second electrode 153. The first electrode 151 may be a conductive oxide, a conductive nitride, or a metal. The first electrode 151 may include a contact layer, and the contact layer may include at least one of, for example, indium tin oxide (ITO), ITO nitride (ITON), indium zinc oxide (IZO), IZO nitride (IZON), aluminum zinc oxide (AZO), aluminum gallium zinc oxide (AGZO), indium zinc tin oxide (IZTO), indium aluminum zinc oxide (IAZO), indium gallium zinc oxide (IGZO), indium gallium tin oxide (IGTO), antimony tin oxide (ATO), gallium zinc oxide (GZO), IZO nitride (IZON), ZnO, IrOx, RuOx, NiO, Au, Cu, Ni, Ti, Ti—W, Cr, W, Pt, V, Fe, and Mo, and may be formed as a single layer or multiple layers.

The second electrode 153 may be disposed on the second conductive semiconductor layer 116b. The second electrode 153 may be electrically connected to the second conductive semiconductor layer 116b. The second electrode 153 may be a conductive oxide, a conductive nitride, or a metal. The second electrode 153 may include a contact layer, and for example, the contact layer may include at least one of ITO, ITON, IZO, IZON, AZO, AGZO, IZTO, IAZO, IGZO, IGTO, ATO, GZO, IZON, ZnO, IrOx, RuOx, NiO, Au, Cu, Ni, Ti, Ti—W, Cr, W, Pt, V, Fe, and Mo and may be formed as a single layer or multiple layers.

The ultraviolet light emitting device 100 of an embodiment may have a full width at half maximum (FWHM) of 17 nm or less. In general, an ultraviolet light emitting device having an FWHM of 20 nm or more destroys DNA, proteins and the like at 300 nm or less, particularly 298 nm or less, so that it is difficult to apply to medical equipment such as an Atopy treatment. In an embodiment, each of the quantum well layers of the active layer 114 may include a thickness of 10 to 25% of the thickness of each of the quantum wall layers to implement an FWHM of 17 nm or less, and thus reliability of the ultraviolet light emitting device applied to the medical equipment may be improved.

In the ultraviolet light emitting device 100 of an embodiment, the EBL 130 is disposed on the active layer 114 to enhance carrier injection efficiency, so that a high current drive of 100 mA or more may be implemented. Specifically, in an embodiment, the first and second intermediate barrier layers 133 and 135 may implement a UVB of 295 to 315 nm of a high current drive of 100 mA or more by the structure of the EBL 130 having a higher Al composition than the first barrier layer 131 and the second barrier layer 137

In an embodiment, the first semiconductor layer 112a, the first superlattice layer 120a, the first conductive type semiconductor layer 112b, and the second superlattice layer 120b between the substrate 101 and the active layer 114 may be included to improve defects, and thus luminous efficiency may be improved.

In an embodiment, the power of light may be improved by the active layer 114 including a quantum well layer having a thickness of 10 to 25% of the thickness of the quantum wall layer.

In an embodiment, reliability may be improved by the first conductive semiconductor layer 116a having a thickness of 40 nm or more.

In an embodiment, the ultraviolet light emitting device 100 having a wavelength of 295 to 315 nm of 100 mA or more may be implemented and applied to a medical equipment such as an Atopy treatment.

FIGS. 9 to 13 are cross-sectional views showing a manufacturing method of an ultraviolet light emitting device according to an embodiment.

Figure 9:
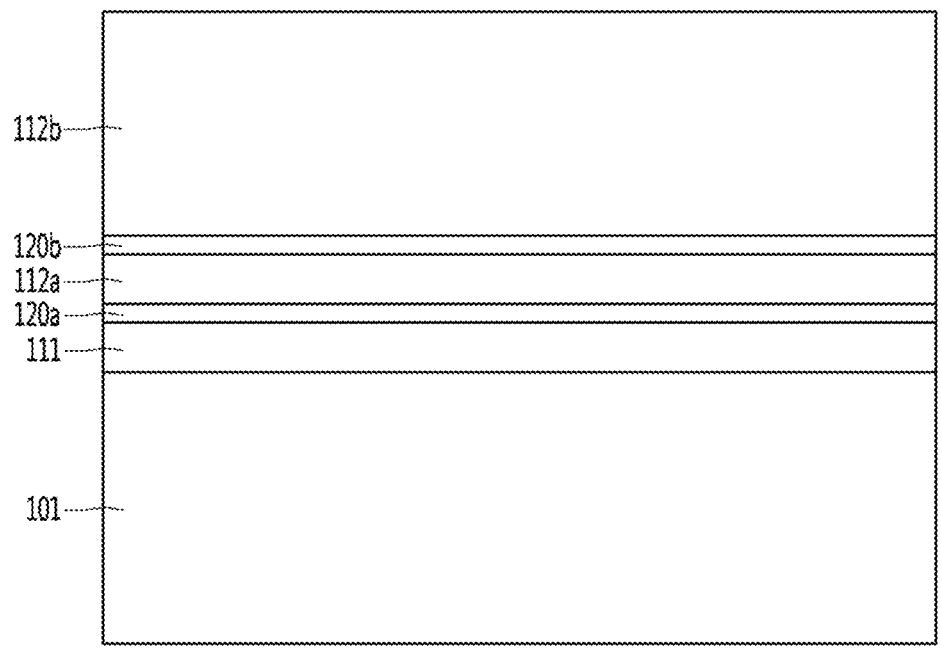
FIGS. 9 to 13 are cross-sectional views showing a method of manufacturing the light emitting device according to an embodiment.

Referring to FIG. 9, in the manufacturing method of the ultraviolet light emitting device according to an embodiment, an AlN template layer 111, a first superlattice layer 120a, a first semiconductor layer 112a, a second superlattice layer 120b, and a first conductive type semiconductor layer 112b may be formed on a substrate 101.

The substrate 101 may be formed of a material having excellent thermal conductivity, and may be a conductive substrate or an insulating substrate. For example, at least one of sapphire ($Al_2O_3$), SiC, Si, GaAs, GaN, ZnO, GaP, InP, Ge, and $Ga_2O_3$ may be used as the substrate 101. A concave-convex structure may be formed on the substrate 101, but is not limited thereto.

The AlN template layer 111, the first superlattice layer 120a, the first semiconductor layer 112a, the second superlattice layer 120b, and the first conductive type semiconductor layer 112b may be formed by a metal organic chemical vapor deposition (MOCVD) method, a chemical vapor deposition (CVD) method, a plasma-enhanced chemical vapor deposition (PECVD) method, a molecular beam epitaxy (MBE) method, and a hydride vapor phase epitaxy (HVPE) method, or the like, but is not limited thereto.

The AlN template layer 111, the first superlattice layer 120a, the first semiconductor layer 112a, the second superlattice layer 120b and the first conductive type semiconductor layer 112b may be grown at a pressure of 100 mbar or less.

The AlN template layer 111 may be formed on the substrate 101. The AlN template layer 111 may include a buffer function. The AlN template layer 111 may alleviate the lattice mismatch between materials of the light emitting structure 110 formed on the AlN template layer 111 and the substrate 101, and the AlN template layer 111 may be formed of at least one of a Group III-V or Group II-VI compound semiconductor such as GaN, InN, InGaN, AlGaN, InAlGaN, and AlInN in addition to AlN.

The first superlattice layer 120a may be disposed on the AlN template layer 111. The first semiconductor layer 112a may be disposed on the first superlattice layer 120a. The second superlattice layer 120b may be disposed on the first semiconductor layer 112a. The first conductive type semiconductor layer 112b may be disposed on the second superlattice layer 120b. The first superlattice layer 120a, the first semiconductor layer 112a, the second superlattice layer 120b and the first conductive type semiconductor layer 112b are gradually reduced in Al composition, and thus lattice mismatch and defects between the AlN template layer 111 and the active layer 114 may be improved.

The first superlattice layer 120a may be formed on the AlN template layer 111. The first superlattice layer 120a is disposed on the AlN template layer 111 so that a function of improving the lattice mismatch and defects between materials of the AlN template layer 111 and the light emitting structure 110 formed on the first superlattice layer 120a may be included. The first superlattice layer 120a may include a first layer 121a and a second layer 121b which are alternately formed in 10 to 20 pairs. The second layer 121b may include a semiconductor material having a composition formula of $Al_xGa_{1-x}N$ ($0.5 \leq x \leq 0.6$). The second layer 121b may include an Al composition of 50% to 60%, and each of the first layer 121a and the second layer 121b may have a thickness of 1 to 5 nm. When the first layer 121a and the second layer 121b are less than 10 pairs in the first superlattice layer 120a, a defect improving effect may be deteriorated. When the first layer 121a and the second layer 121b are more than 20 pairs in the first superlattice layer 120a, crystallinity may be lowered due to a difference in lattice constant. The second layer 121b may be a first conductive type AlGaN. The second layer 121b may be an unintentionally doped GaN. For example, the second layer 121b may be AlGaN unintentionally having a first conductive type during a growth process.

The first semiconductor layer 112a may be formed on the first superlattice layer 120a. The first semiconductor layer 112a may be implemented as a compound semiconductor such as a Group III-V or Group II-VI. For example, the first semiconductor layer 112a may be formed of any one or more of GaN, InN, AlN, InGaN, AlGaN, InAlGaN, AlInN, AlGaAs, InGaAs, AlInGaAs, GaP, AlGaP, InGaP, AlInGaP and InP. The first semiconductor layer 112a of an embodiment may include a semiconductor material having a composition formula of $Al_yGa_{1-y}N$ ($0.5 \leq y \leq 0.6$). The first semiconductor layer 112a of an embodiment may include an Al composition of 50 to 60%, and the thickness of the first semiconductor layer 112a of an embodiment may be 10 to 1000 nm. In an embodiment, the first semiconductor layer 112a having a thickness of 200 nm will be described as an example. The first semiconductor layer 112a may be doped with a first conductive type dopant. When the first conductive type dopant is an n-type dopant, the first conductive type dopant may include Si, Ge, Sn, Se, or Te as an n-type dopant, but is not limited thereto.

The second superlattice layer 120b may be formed on the first semiconductor layer 112a. The second superlattice layer 120b may be disposed on the first semiconductor layer 112a to include a function of improving lattice mismatch and defects between materials of the first semiconductor layer 112a and the light emitting structure 110 formed on the second superlattice layer 120b. The second superlattice layer 120b may include a third layer 123a and a fourth layer 123b which are alternately formed in 10 to 20 pairs.

The third layer 123a may include a semiconductor material having a composition formula of $Al_aGa_{1-a}N$ ($0.5 \leq a \leq 0.6$). The third layer 123a may include an Al composition of 50 to 60%. The thickness of each of the third layers 123a of an embodiment may be 1 to 5 nm. The aluminum composition of the third layer 123a may be disposed within the composition range of aluminum of the first semiconductor layer 112a. Accordingly, lattice mismatch and defects on the first semiconductor layer 112a may be improved.

The fourth layer 123b may include a semiconductor material having a composition formula of $Al_bGa_{1-b}N$ ($0.45 \leq b \leq 0.55$). The fourth layer 123b may include an Al composition of 45 to 55%. The thickness of each of the fourth layers 123b of an embodiment may be 1 to 5 nm. The fourth layer 123b may have a lower aluminum composition than that of the third layer 123a. At least one or both of the third and fourth layers 123a and 123b may include a first conductive type dopant. Here, when the first conductive type dopant is an n-type dopant, the first conductive type dopant may include Si, Ge, Sn, Se, or Te as an n-type dopant, but is not limited thereto. In an embodiment, the Al composition gradually decreases from the AlN template layer 111 to the active layer 114, and thus crystallinity may be improved.

The first conductive type semiconductor layer 112b may be formed on the second superlattice layer 120b. The first conductive type semiconductor layer 112b may be implemented as a compound semiconductor such as a Group III-V or Group II-VI. For example, the first conductive type semiconductor layer 112b may be formed of any one or more of GaN, InN, AlN, InGaN, AlGaN, InAlGaN, AlInN, AlGaAs, InGaAs, AlinGaAs, GaP, AlGaP, InGaP, AlInGaP and InP. The first conductive type semiconductor layer 112b may have a lower Al composition than that of the first semiconductor layer 112a, the second layer 121b, and the third layer 123a. The Al composition of the first conductive type semiconductor layer 112b may be the same as the Al composition range of the fourth layer 123b.

The first conductive type semiconductor layer 112b of an embodiment may include a semiconductor material having a composition formula of $Al_zGa_{1-z}N$ ($0.45 \leq z \leq 0.55$). The first conductive type semiconductor layer 112b of an embodiment may include an Al composition of 45 to 55%, and the thickness of the first conductive type semiconductor layer 112b of an embodiment may be 500 to 1000 nm. In an embodiment, the first conductive type semiconductor layer 112b having a thickness of 1000 nm will be described as an example. The first conductive type semiconductor layer 112b may be doped with a first conductive type dopant. When the first conductive type dopant is an n-type dopant, the first conductive type dopant may include Si, Ge, Sn, Se, or Te as an n-type dopant, but is not limited thereto.

Figure 10:
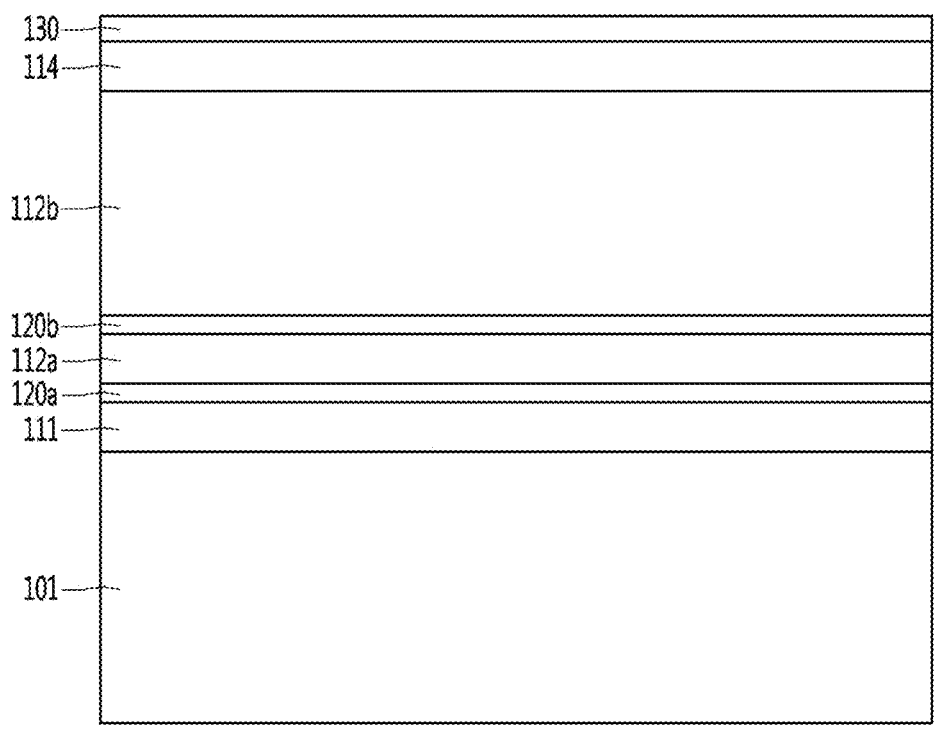

Referring to FIG. 10, the active layer 114 may be disposed on the first conductive type semiconductor layer 112b, and the EBL 130 may be disposed on the active layer 114. The active layer 114 and the EBL 130 may be formed by a method such as MOCVD, CVD, PECVD, MBE, HVPE, or the like, but is not limited thereto.

The formation conditions of the active layer 114 and the EBL 130 may improve light power and improve light efficiency.

The active layer 114 may be formed as at least one of a single quantum well structure, a multi-quantum well (MQW) structure, a quantum-wire structure, and a quantum dot structure. The active layer 114 is a layer at which electrons (or holes) injected through the first conductive type semiconductor layer 112b encounters holes (or electrons) injected through the first conductive semiconductor layer 116a and light is emitted by a band gap difference of an energy band according to a formation material of the active layer 114.

The active layer 114 may be composed of a compound semiconductor. The active layer 114 may be implemented as at least one of compound semiconductors such as a Group III-V or Group II-VI. The active layer 114 may include a quantum well layer and a quantum wall layer. When the active layer 114 is implemented as an MQW structure, the quantum well layer and the quantum wall layer may be alternately disposed. The quantum well layer and the quantum wall layer may be formed in a structure of any one or more pairs of AlGaN/GaN, AlGaN/AlGaN, InGaN/GaN, InGaN/InGaN, InAlGaN/GaN, GaAs/AlGaAs, InGaAs/AlGaAs, GaP/AlGaP, and InGaP/AlGaP, but are not limited thereto.

In the active layer 114 of an embodiment, the thickness of each of the quantum well layers may be 10 to 25% of the thickness of each of the quantum wall layers. Referring to FIG. 6, the active layer 114 of an embodiment may improve the power of light by a quantum well layer structure having a thickness of 10 to 25% of the quantum wall layer. For example, each of the quantum well layers may be 1.5 to 2.5 nm. FIG. 6 is a graph showing the power of light according to the thickness of the quantum well layer of the active layer 114 having the quantum wall layer of 10.9 nm, and shows the highest light power in the quantum well layer having the thickness of 2.1 nm.

The EBL 130 may be formed on the active layer 114. The EBL 130 may include a second dopant. The EBL 130 of an embodiment may include a plurality of barrier layers 131, 133, 135, and 137, and a plurality of well layers 132, 134, and 136. The EBL 130 may be formed of a Group III-V or II-VI compound semiconductor, for example, the EBL 130 may be formed of three or more pairs of AlGaN/AlGaN, but is not limited thereto. The EBL 130 may be doped with a second conductive type dopant. For example, when the EBL 130 is a p-type semiconductor layer, the second conductive type dopant may include Mg, Zn, Ca, Sr, or Ba as a p-type dopant. The EBL 130 of an embodiment may include a function for increasing a carrier provided to the active layer 114 to implement a UVB of 295 to 315 nm of a high current drive of 100 mA or more. In addition, the EBL 130 may include an electron blocking function for blocking electrons, and thus luminous efficiency may be improved. For this, the EBL 130 including the second conductive type dopant of an embodiment may be formed such that a plurality of barrier layers 131, 133, 135, and 137 and a plurality of well layers 132, 134, and 136 are alternated in three pairs. The plurality of barrier layers 131, 133, 135, and 137 and the plurality of well layers 132, 134, and 136 of an embodiment may improve luminous efficiency by the Al composition and thickness.

Some layers of the EBL 130 may include a high Al composition based on an energy level reference (REF) of the last quantum wall layer of the active layer 114. For example, the last quantum wall layer of the active layer 114 may include an Al composition of 50%, and the plurality of barrier layers 131, 133, 135, and 137 may include an Al composition of at least 45% or more. Here, the plurality of barrier layers 131, 133, 135, and 137 may include a higher Al composition than that of the plurality of well layers 132, 134, and 136 and may include a higher Al composition than that of the last quantum wall layer of the active layer 114. The Al composition of the EBL 130 may block electrons and confine holes to improve luminous efficiency by increasing carrier injection of the active layer 114.

The plurality of barrier layers 131, 133, 135, and 137 may include a first barrier layer 131 in contact with the active layer 114, a second barrier layer 137 in contact with the first conductive semiconductor layer 116a, and first and second intermediate barrier layers 133 and 135 disposed between the first barrier layer 131 and the second barrier layer 137. Here, any one of the first and second intermediate barrier layers 133 and 135 may be omitted, or may be a plurality of three or more. The plurality of well layers 132, 134, and 136 may include a first well layer 132 between the first barrier layer 131 and the first intermediate barrier layer 133, a second well layer 134 between the first and second intermediate barrier layers 133 and 135, and a third well layer 136 between the second intermediate barrier layer 135 and the second barrier layer 137.

The first barrier layer 131 may have a higher Al composition than that of the last quantum wall layer of the active layer 114. For example, the first barrier layer 131 may include a semiconductor material having a composition formula of $Al_pGa_{1-p}N$ ($0.50 \leq p \leq 0.74$). The first barrier layer 131 of an embodiment may include an Al composition of 50 to 74%, and a thickness W1 of the first barrier layer 131 of an embodiment may be greater than a thickness W2 of the first well layer 132. The thickness W1 of the first barrier layer 131 of an embodiment may be 3 to 10 nm.

The second barrier layer 137 may have a higher Al composition than that of the first conductive semiconductor layer 116a. For example, the second barrier layer 137 may include a semiconductor material having a composition formula of $Al_qGa_{1-q}N$ ($0.50 \leq q \leq 0.74$). The second barrier layer 137 of an embodiment may include an Al composition of 50 to 74% and a thickness W7 of the second barrier layer 137 of an embodiment may be greater than a thickness W6 of the third well layer 136. The thickness W7 of the second barrier layer 137 of an embodiment may be 3 to 10 nm.

The first and second intermediate barrier layers 133 and 135 may have a higher Al composition than that of the first barrier layer 131 and the second barrier layer 137. The EBL 130 of an embodiment may improve hole injection. For example, the EBL 130 may improve luminous efficiency by confining holes in the first and second intermediate barrier layers 133 and 135 to increase carrier injection of the active layer 114. The first and second intermediate barrier layers 133 and 135 may include a semiconductor material having a composition formula of $Al_rGa_{1-r}N$ ($0.55 \leq r \leq 0.74$). The first and second intermediate barrier layers 133 and 135 of an embodiment may include an Al composition of 55 to 74%. Thicknesses W3 and W5 of the first and second intermediate barrier layers 133 and 135 of an embodiment may be thicker than a thickness W4 of the second well layer 134. The thicknesses W3 and W5 of the first and second intermediate barrier layers 133 and 135 of an embodiment may be 3 to 10 nm. Specifically, in the EBL 130 including the first barrier layer 131 and the second barrier layer 137 having an Al composition of 54% and the first and second intermediate barrier layers 133 and 135 having a composition of 64%, the output voltage may be improved by 30% or more as compared with a general ultraviolet light emitting device.

The plurality of well layers 132, 134 and 136 may include the first well layer 132 between the first barrier layer 131 and the first intermediate barrier layer 133, the second well layer 134 between the first and second intermediate barrier layers 133 and 135, and the third well layer 136 between the second intermediate barrier layer 135 and the second barrier layer 137.

The first well layer 132 may include a lower Al composition than that of the last quantum wall layer 114a (see FIG. 4) of the active layer 114. The first well layer 132 may include a semiconductor material having a composition formula of $Al_eGa_{1-e}N$ ($0.24 \leq e \leq 0.45$). The thickness W2 of the first well layer 132 of an embodiment may be thinner than the thickness W1 of the first barrier layer 131 and the thickness W3 of the first intermediate barrier layer 133. The thickness W2 of the first well layer 132 of an embodiment may be 1 to 5 nm.

The second well layer 134 may include a lower Al composition than the Al composition of the last quantum wall layer of the active layer 114. The second well layer 134 may include a semiconductor material having a composition formula of $Al_fGa_{1-f}N$ ($0.24 \leq f \leq 0.48$). The thickness W4 of the second well layer 134 of an embodiment may be thinner than the thicknesses W3 and W5 of the first and second intermediate barrier layers 133 and 135. The thickness W4 of the second well layer 134 of an embodiment may be 1 to 5 nm.

The third well layer 136 may include a lower Al composition than that of the last quantum wall layer of the active layer 114. The third well layer 136 may include a semiconductor material having a composition formula of $Al_gGa_{1-g}N$ ($0.24 \leq g \leq 0.48$). The thickness W6 of the third well layer 136 of an embodiment may be thinner than the thickness W5 of the second intermediate barrier layer 135 and the thickness W7 of the second barrier layer 137. The thickness W6 of the third well layer 136 of an embodiment may be 1 to 5 nm. The second and third well layers 134 and 136 may have the same Al composition and thickness, but are not limited thereto.

In an embodiment, the EBL 130 may be disposed on the active layer 114 to improve carrier injection efficiency, and thus the luminous efficiency may be improved. An embodiment may be implemented as a UVB of 295 to 315 nm of a high current drive of 100 mA or more.

Figure 11:
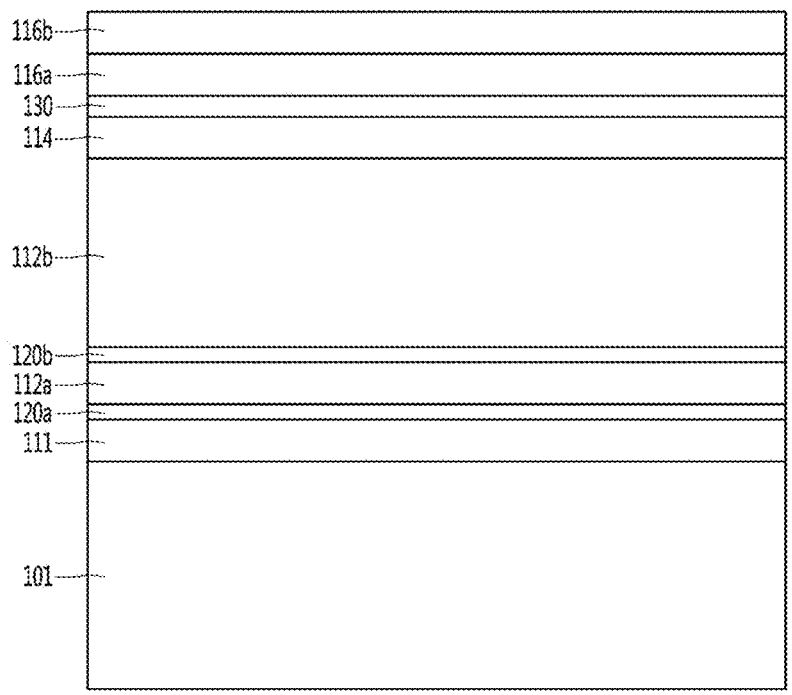

Referring to FIG. 11, a first conductive semiconductor layer 116a and a second conductive semiconductor layer 116b may be formed on the EBL 130. The first conductive semiconductor layer 116a and the second conductive semiconductor layer 116b may be formed by a method such as MOCVD, CVD, PECVD, MBE, HVPE, or the like, but is not limited thereto.

The first conductive semiconductor layer 116a and the second conductive semiconductor layer 116b may be grown at a pressure between the first conductive type semiconductor layer 112b and the EBL 130. For example, the first conductive semiconductor layer 116a and the second conductive semiconductor layer 116b may be grown at a pressure of 450 mbar, but are not limited thereto.

The first conductive semiconductor layer 116a a may be formed on the EBL 130. The first conductive semiconductor layer 116a may be implemented as a compound semiconductor such as a Group III-V or Group II-VI. For example, the first conductive semiconductor layer 116a may be formed of any one or more of GaN, InN, AlN, InGaN, AlGaN, InAlGaN, AlInN, AlGaAs, InGaAs, AlInGaAs, GaP, AlGaP, InGaP, AlInGaP and InP. The first conductive semiconductor layer 116a of an embodiment may include a semiconductor material having a composition formula of $Al_sGa_{1-s}N$ ($0.20 \leq s \leq 0.45$). The first conductive semiconductor layer 116a may include an Al composition of 20 to 45%. A thickness of the first conductive semiconductor layer 116a may be 40 nm or more. FIG. 7 is a graph showing reliability according to a thickness of a first conductive semiconductor layer of an embodiment. Referring to FIG. 7, when the first conductive semiconductor layer 116a of an embodiment has a thickness of 40 nm or more, a change of an output voltage with time is constant, and thus reliability may be improved. The thickness of the first conductive semiconductor layer 116a of an embodiment may be 40 to 300 nm. The first conductive semiconductor layer 116a may be doped with a second conductive type dopant. In the case in which the first conductive semiconductor layer 116a is a p-type semiconductor layer, the second conductive type dopant may include Mg, Zn, Ca, Sr, or Ba as a p-type dopant.

The second conductive semiconductor layer 116b may be formed on the first conductive semiconductor layer 116a. The second conductive semiconductor layer 116b may be disposed between the first conductive semiconductor layer 116a and the second electrode 153 (see FIG. 2) for ohmic contact between the first conductive semiconductor layer 116a and the second electrode 153 (see FIG. 2). The second conductive semiconductor layer 116b may be a GaN including a first conductive type dopant for ohmic contact between the first conductive semiconductor layer 116a and the second electrode 153 (see FIG. 2), but is not limited thereto. The second conductive semiconductor layer 116b may be flat on the surface directly contacting the second electrode 153 (see FIG. 2). For this, the second conductive semiconductor layer 116b may be formed by a 2D growth method. FIG. 8 is a view showing a surface of a second conductive semiconductor layer of an embodiment. The second conductive semiconductor layer 116b of an embodiment may be implemented as a flat surface by 2D growth to improve reliability of contact with the second electrode 153 (see FIG. 2).

Figure 12:
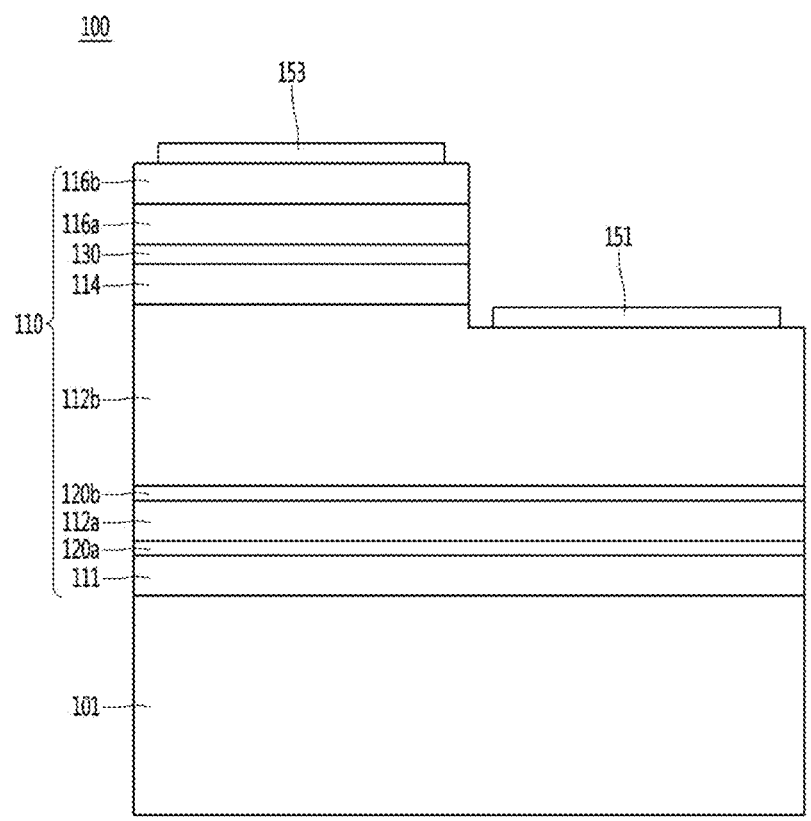

Referring to FIG. 12, the first and second electrodes 151 and 153 may be formed on the light emitting structure 110. In the light emitting structure 110, a part of the first conductive type semiconductor layer 112b may be exposed via mesa etching from the active layer 114, the EBL 130, the first conductive semiconductor layer 116a, and the second conductive semiconductor layer 116b.

The first electrode 151 may be formed on the exposed first conductive type semiconductor layer 112b. The first electrode 151 may be electrically connected to the first conductive type semiconductor layer 112b. The first electrode 151 may be electrically insulated from the second electrode 153.

The second electrode 153 may be formed on the second conductive semiconductor layer 116b. The second electrode 153 may be electrically connected to the second conductive semiconductor layer 116b.

The first and second electrodes 151 and 153 may be a conductive oxide, a conductive nitride, or a metal. For example, the first and second electrodes 151 and 153 may include at least one of indium tin oxide (ITO), ITO nitride (ITON), indium zinc oxide (IZO), IZO nitride (IZON), aluminum zinc oxide (AZO), aluminum gallium zinc oxide (AGZO), indium zinc tin oxide (IZTO), indium aluminum zinc oxide (IAZO), indium gallium zinc oxide (IGZO), indium gallium tin oxide (IGTO), antimony tin oxide (ATO), gallium zinc oxide (GZO), IZO nitride (IZON), ZnO, IrOx, RuOx, NiO, Au, Cu, Ni, Ti, Ti—W, Cr, W, Pt, V, Fe, and Mo, and may be formed as a single layer or multiple layers.

Figure 13:
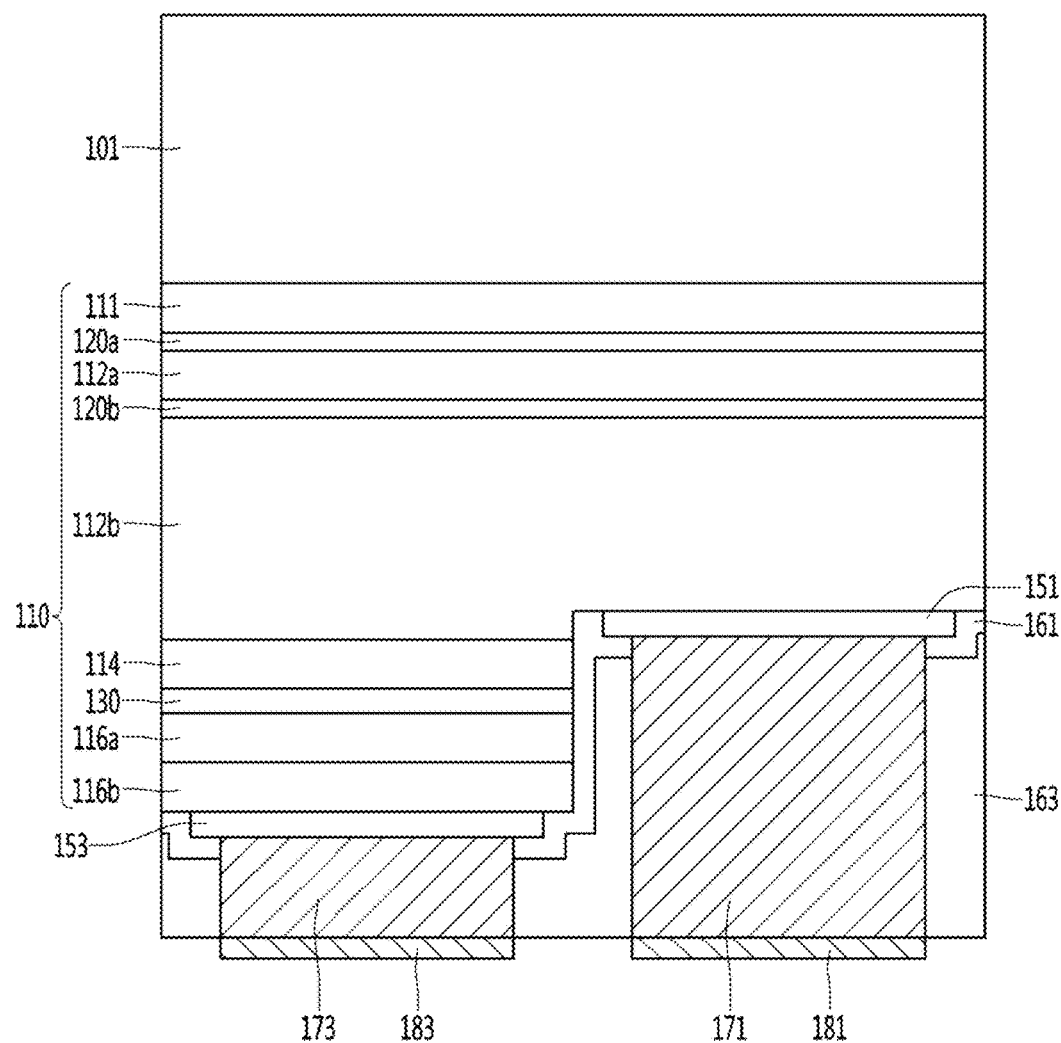

Referring to FIG. 13, an embodiment may be a flip chip structure in which the first and second electrodes 151 and 153 are disposed at a lower portion. A first insulating layer 161 may expose a part of lower surfaces of the first and second electrodes 151 and 153, and formed on the light emitting structure 110. The first insulating layer 161 may be in contact with a lower portion of the light emitting structure 110 in which the first and second electrodes 151 and 153 are disposed.

First and second connection electrodes 171 and 173 may be formed on the lower surfaces of the first and second electrodes 151 and 153 exposed from the first insulating layer 161. The first and second connection electrodes 171 and 173 may be formed by a plating process, but are not limited thereto. The first insulating layer 161 may be an oxide or a nitride. For example, the first insulating layer 161 may be at least one selected from the group consisting of $SiO_2$, $Si_xO_y$, $Si_3N_4$, $Si_xN_y$, $SiO_xN_y$, $Al_2O_3$, $TiO_2$, AlN, and the like.

The first and second connection electrodes 171 and 173 may be a metal including at least one of Ag, Ni, Al, Rh, Pd, Ir, Ru, Mg, Zn, Pt, Cu, Au and Hf, or an alloy thereof. The first and second connection electrodes 171 and 173 may be formed as a single layer or multiple layers including the metal or the alloy and a transparent conductive material, such as ITO, IZO, IZTO, IAZO, IGZO, IGTO, AZO, or ATO.

A second insulating layer 163 may be formed under the first insulating layer 161 and in direct contact with the first insulating layer 161. The second insulating layer 163 may expose lower portions of the first and second connection electrodes 171 and 173, and may be formed on side portions of the first and second connection electrodes 171 and 173. The second insulating layer 163 may be formed by adding a heat diffusing agent in a resin such as silicone or epoxy. The heat diffusing agent may include at least one material of oxides, nitrides, fluorides, and sulfides, for example, a ceramic material having a material such as Al, Cr, Si, Ti, Zn, and Zr. The heat diffusing agent may be defined as a powder particle, a grain, a filler, or an additive having a predetermined size. The second insulating layer 163 may be omitted.

First and second pads 181 and 183 may be formed on the first and second connection electrodes 171 and 173 exposed from the second insulating layer 163. The first and second pads 181 and 183 may be a metal including at least one of Ag, Ni, Al, Rh, Pd, Ir, Ru, Mg, Zn, Pt, Cu, Au and Hf, or an alloy thereof. The first and second pads 181 and 183 may be formed as a single layer or multiple layers including the metal or the alloy and a transparent conductive material, such as ITO, IZO, IZTO, IAZO, IGZO, IGTO, AZO, or ATO.

An embodiment includes the substrate 101 disposed on the first conductive type semiconductor layer 112b, but is not limited thereto. For example, the substrate 101 may be removed by a laser lift off (LLO) process. Here, the LLO process is a process such that laser is irradiated to a lower surface of the substrate 101 to separate the substrate 101 and the light emitting structure 110 from each other. In the light emitting device 100 according to an embodiment, the substrate 101 and the AlN template layer 111 may be removed, but are not limited thereto.

The ultraviolet light emitting device 100 of an embodiment may have a full width at half maximum (FWHM) of 17 nm or less. In general, an ultraviolet light emitting device having an FWHM of 20 nm or more destroys DNA, proteins and the like at 300 nm or less, particularly 298 nm or less, so that it is difficult to apply to medical equipment such as an Atopy treatment. In an embodiment, each of the quantum well layers of the active layer 114 may include a thickness of 10 to 25% of each of the quantum walls to implement an FWHM of 17 nm or less, and thus reliability of the ultraviolet light emitting device applied to the medical equipment may be improved.

The active layer 114 and the EBL 130 of an embodiment may improve light power and improve light efficiency.

In an embodiment, the EBL 130 is disposed on the active layer 114 to improve carrier injection efficiency, thereby implementing a high current drive of 100 mA or more. Specifically, in an embodiment, the first and second intermediate barrier layers 133 and 135 may implement a UVB of 295 to 315 nm of a high current drive of 100 mA or more by the structure of the EBL 130 having a higher Al composition than the first barrier layer 131 and the second barrier layer 137.

In an embodiment, the first semiconductor layer 112a, the first superlattice layer 120a, the first conductive type semiconductor layer 112b, and the second superlattice layer 120b may be included between the substrate 101 and the active layer 114 to improve defects, and thus luminous efficiency can be improved.

In an embodiment, power of light may be improved by the active layer 114 including the quantum well layer having a thickness of 10 to 25% of a thickness of the quantum wall.

In an embodiment, reliability may be improved by the first conductive semiconductor layer 116a having a thickness of 40 nm or more.

Figure 14:
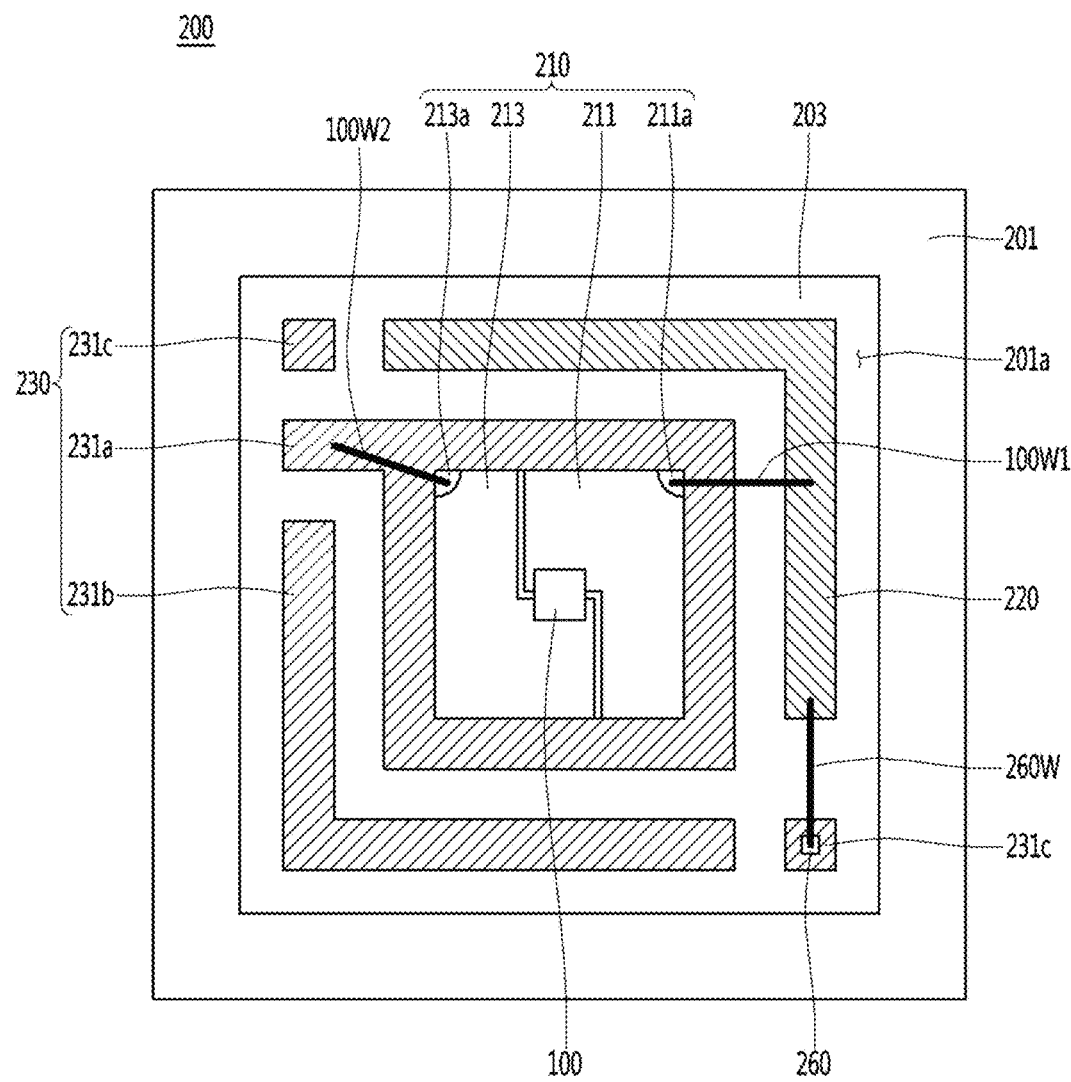
FIG. 14 is a plan view showing a light emitting device package having the light emitting device according to an embodiment.

FIG. 14 is a plan view showing a light emitting device package according to an embodiment.

As shown in FIG. 14, a light emitting device package 200 of an embodiment may include a light emitting device 100, a package body 201, a heat dissipation frame 210, a protection device 260, first and second lead frames 220 and 230.

The package body 201 may include at least one of a light-transmitting material, a reflective material, and an insulating material. The package body 201 may include a material having reflectance higher than transmittance with respect to light emitted from the light emitting device 100. The package body 201 includes an insulating material such as a ceramic material. The ceramic material includes a low temperature co-fired ceramic (LTCC) or a high temperature co-fired ceramic (HTCC) which is co-fired at the same time. The material of the package body 201 may be, for example, AlN, and may be formed of a metal nitride having a thermal conductivity of 140 W/mK or more. The package body 201 may be a resin-based insulating material. For example, the package body 201 may be formed of at least one of a resin material such as a polyphthalamide (PPA), epoxy or silicone material, silicon (Si), a metal material, photosensitive glass (PSG), sapphire (Al$_2$O$_3$), and a printed circuit board (PCB). The package body 201 may have, for example, a square shape, when viewed from the top but is not limited thereto. The top view of the package body 201 may be a circular shape or a polygonal shape.

The package body 201 may be coupled to the first and second lead frames 220 and 230. The package body 201 may include a cavity 203 exposing a part of upper surfaces of the first and second lead frames 220 and 230. The cavity 203 may be formed as a recess in which an upper portion of the package body 201 is concave or depressed. The cavity 203 may expose a part of the upper surface of the first lead frame 220 and may expose a part of the upper surface of the second lead frame 230. The first and second lead frames 220 and 230 may be disposed at a bottom of the cavity 203. The first and second lead frames 220 and 230 may be disposed to be spaced apart from each other at the bottom of the cavity 203 and at least a part thereof may extend into the package body 201 or extend to a bottom of the package body 201 via a via structure. The first lead frame 220 may include a bent shape that is adjacent to at least two side surfaces of the cavity 203 and extends along two adjacent side surfaces. The second lead frame 230 includes a first lead portion 231a in which the light emitting device 100 is disposed, a second lead portion 231b disposed outside the first lead portion 231a, and a third lead portion 231c. A top surface area of the first lead portion 231a may be larger than that of the first lead frame 220, and thus heat dissipation efficiency may be improved. The first lead portion 231a may be disposed between the second lead portion 231b and the first lead frame 220. The first lead portion 231a may be disposed at a bottom center of the cavity 203. The first lead portion 231a may be electrically connected to the light emitting device 100 via a wire 100W2. The second lead portion 231b may be disposed at the opposite side of the first lead frame 220 with respect to the light emitting device 100 and may have a bent shape along other two side surfaces. At least one of the second lead portion 231b and the first lead frame 220 may be connected to the light emitting device 100 with a wire.

The light emitting device 100 according to an embodiment may be disposed at the bottom of the cavity 203. A protection device 260 for protecting the light emitting device 100 may be disposed in the cavity 203.

The first lead portion 231a may be exposed to a center area of the cavity 203, the second lead portion 231b may be diagonally symmetric with the first lead frame 220 to correspond to the shape of the first lead frame 220, and the third lead portion 231c may be disposed at an edge region and a diagonal edge region of the cavity 203 in which the protection device 260 is mounted. The first to third lead portions 231a, 231b, and 131c may be exposed at the bottom surface of the cavity 203 and the shape including the area and the width of the upper surface of the second lead frame 230 may be variously changed.

The first and second lead frames 220 and 230 may be spaced apart from each other at a predetermined distance and coupled with the package body 201. The light emitting device 100 according to an embodiment may be disposed on the second lead frame 230. In the first lead frame 220, a first wire 100W1 connected to the light emitting device 100 may be connected. The protection device 260 may be disposed on the third lead portion 231c of the second lead frame 230 and may be connected to the first lead frame 220 with a wire 260W. The third lead portion 231c may be disposed in one or a plural and may be disposed to be spaced apart from both ends of the first lead frame 220 at a predetermined distance.

The third lead portion 231c may be disposed at a lower depth than the bottom of the cavity 203 to reduce optical loss by the protection device 260 when the protection device 260 is disposed. The first lead frame 220 may have a diagonal bent structure that is symmetrical with the second lead portion 231b, but is not limited thereto.

The first and second lead frames 220 and 230 may include a conductive material. For example, the first and second lead frames 220 and 230 may include at least one of titanium (Ti), copper (Cu), nickel (Ni), gold (Au), chromium (Cr), tantalum (Ta) tin (Sn), silver (Ag), phosphorous (P), iron (Fe), tin (Sn), zinc (Zn), and aluminum (Al), any may be formed of a plurality of layers. For example, the first and second lead frames 220 and 230 of an embodiment may be composed of a base layer including copper (Cu) and an antioxidant layer including silver (Ag) covering the base layer, but are not limited thereto.

The heat dissipation frame 210 may include first and second lead electrodes 211 and 213, the first lead electrode 211 may include a first pad part 211a connected to the first wire 100W1, and the second lead electrode 213 may include a second pad part 213a connected to the second wire 100W2. In the heat dissipation frame 210, the first and second lead electrodes 211 and 213 are disposed on a ceramic body or an insulating material body and the light emitting device 100 according to an embodiment is disposed on the first and second lead electrodes 211 and 213. The light emitting device 100 may be flip-chip bonded to the first and second lead electrodes 211 and 213, or may be connected with one or more wires. The first and second lead electrodes 211 and 213 may have an area larger than that of the light emitting device 100 on the body of the heat dissipation frame 210 to improve heat dissipation efficiency and to be thermally conducted via the package body 201. The heat dissipation frame 210 may be adhered to the bottom of the cavity 203 with an adhesive, but is not limited thereto.

The light emitting device 100 may be mounted on the heat dissipation frame 210. The light emitting device 100 may include the technical features of FIGS. 1 to 13.

The protection device 260 may be disposed on the third lead portion 231c. The protection device 260 may be disposed on the upper surface of the second lead frame 230 exposed from the package body 201. The protection device 260 may be a Zener diode, a thyristor, a transient voltage suppression (TVS), or the like, but is not limited thereto. The protection device 160 of an embodiment will be described as a Zener diode that protects the light emitting device 100 from electrostatic discharge (ESD). The protection device 260 may be connected to the first lead frame 220 via a wire.

Figure 15:
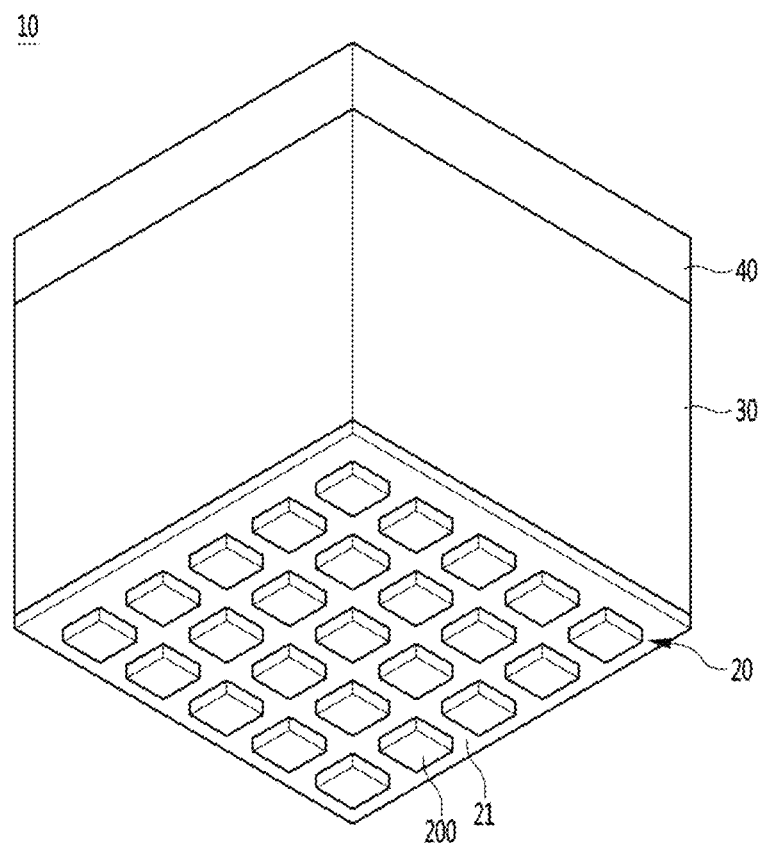
FIG. 15 is a perspective view showing a light emitting module having the light emitting device package according to an embodiment.
Figure 16:
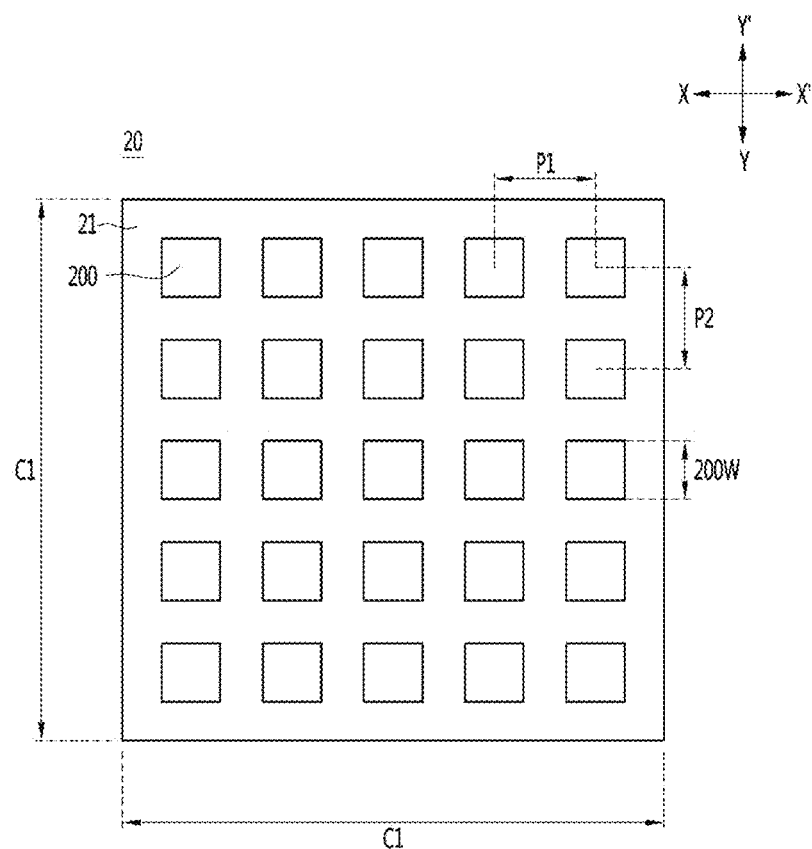
FIG. 16 is a plan view showing a light emitting unit of the light emitting module of FIG. 15.
Figure 17:
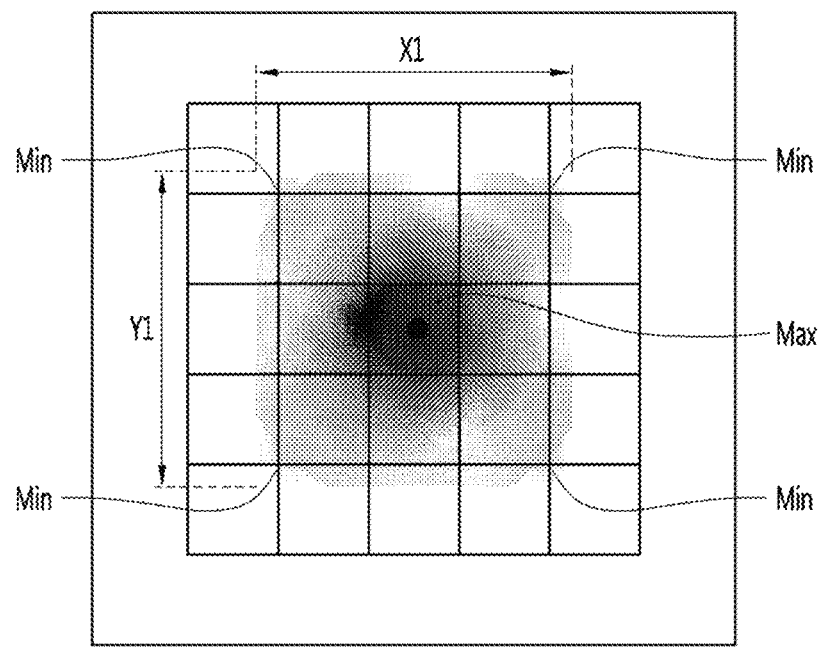
FIG. 17 is a diagram showing light uniformity of the light emitting module of FIG. 16.

FIG. 15 is a perspective view showing a light emitting module having the light emitting device of FIG. 1 or the light emitting device package of FIG. 14 according to an embodiment, FIG. 16 is a plan view showing a light emitting unit of the light emitting module of FIG. 15, and FIG. 17 is a diagram showing light uniformity of the light emitting module of an embodiment.

As shown in FIGS. 15 and 16, a light emitting module 10 of an embodiment may include a light emitting unit 20, and first and second heat dissipation parts 30 and 40. An embodiment limits the configuration of the first and second heat dissipation parts 30 and 40, but is not limited thereto. An embodiment is required to have a highly reliable light emitting module 10 for medical treatment with a highly efficient UVB wavelength. In addition, as shown in FIG. 17, it is required to have a light emitting module 10 capable of implementing light uniformity of a target region TA at 70% or more, and at the same time, reducing the number of the light emitting device packages 200, thereby reducing an overall size and manufacturing costs. For this, an embodiment may have a high current drive of 200 mA or more and a full width at half maximum (FWHM) of 17 nm or less, and the light emitted from the light emitting unit 20 may have a uniformity of 70% or more at the target region TA. Here, the uniformity may be defined as minimum illumination (Min)/maximum illumination (Max) with respect to a center region where the illuminance is maximized and an edge region where the illuminance is minimized in the target region.

As shown in FIGS. 15 and 16, the first heat dissipation part 30 may be disposed at a rear surface of the light emitting unit 20. The first heat dissipation part 30 may be in direct contact with the light emitting unit 20 and may emit heat generated from the light emitting unit 20. The first heat dissipation part 30 may be, for example, a heat sink, but is not limited thereto. The first heat dissipation part 30 may include a plurality of heat dissipation fins. Here, the plurality of heat dissipation fins may increase the heat dissipation area to improve the heat dissipation efficiency.

The second heat dissipation part 40 may be disposed at a rear surface of the first heat dissipation part 30. The second heat dissipation part 40 may be in direct contact with the first heat dissipation part 30. The second heat dissipation part 40 may include a function of dissipating the heat transferred at the first heat dissipation part 30 to the outside. For example, the second heat dissipation part 40 may include a cooling fan using air convection, but is not limited thereto.

The light emitting unit 20 of an embodiment may include a circuit board 21 and a plurality of light emitting device packages 200. The plurality of light emitting device packages 200 may be mounted at a front surface of the circuit board 21. Here, the circuit board 21 may be in contact with the first heat dissipation part 30 at a rear surface thereof. In a size of the circuit board 21, a length C1 in a first direction may be the same as or different from a length C2 in a second direction. The lengths C1 and C2 of the circuit board 21 may be four or five times a length 200 W of the light emitting device package 200. The circuit board 21 may include a resin-based printed circuit board (PCB), a metal core PCB, a flexible PCB, a ceramic PCB, and an FR-4 substrate.

The plurality of light emitting device packages 200 may emit a UVB wavelength of 300 to 320 nm, which is driven by a high current of 100 mA or more. Specifically, the plurality of light emitting device packages 200 may implement an effective wavelength for optical therapy (300 to 320 nm) having a full width at half maximum (FWHM) of 17 nm or less. In general, an ultraviolet light emitting device having an FWHM of 20 nm or more destroys DNA, proteins and the like at 300 nm or less, particularly 298 nm or less, so that it is difficult to apply to medical equipment such as an Atopy treatment. The light emitting device package 200 of an embodiment may implement a full width at half maximum (FWHM) of 17 nm or less to improve reliability of the light emitting module 10 for optical therapy.

As shown in FIGS. 16 and 17, the light emitting module 10 of an embodiment may implement a light uniformity of 70% or more in a target region TA in which light of an ultraviolet wavelength emitted from the light emitting device package 200 is projected. The light uniformity may be defined as minimum illumination (Min)/maximum illumination (Max) with respect to a center region where the illuminance is maximized and an edge region where the illuminance is minimized in the target region TA. For example, the target region TA may be spaced apart from the light emitting unit 20 of the light emitting module 10 at 20 mm and have widths Y1 and X1 of 30 mm, but is not limited thereto. The target region TA may have widths Y1 and X1 of 10 to 30 mm. Specifically, the target region TA for an optical therapy may have a uniformity of 70% or more, which is defined as a minimum illumination (Min)/a maximum illumination (Max), and a minimum Min illumination of 10 $mW/cm^2$ or more. When the light uniformity is less than 70%, reliability of optical therapy may be deteriorated due to a difference in illumination between the center portion and the edge region of the target region TA.

The plurality of light emitting device packages 200 may have a first pitch P1 in a first direction X-X' and may have a second pitch P2 in a second direction Y-Y' orthogonal to the first direction X-X'. The first and second pitches P1 and P2 may be 30 to 50% of the widths Y1 and X1 of the target region TA. The first and second pitches P1 and P2 may be 10 mm or more. The first and second pitches P1 and P2 may be 10 to 15 mm. The first and second pitches P1 and P2 may be the same, but are not limited thereto. For example, the first and second pitches P1 and P2 may be different from each other. For example, an embodiment may include 25 light emitting device packages 200 having first and second pitches P1 and P2 of 10 mm in order to implement a uniformity of 70% or more in a target region TA spaced apart at 20 mm and having widths Y1 and X1 of 30 mm. Here, each of light emitting device packages 200 may have a luminous intensity Po of 10 mW or more. A detailed description of the light emitting device package 200 will be described with reference to FIGS. 6 to 19.

An embodiment may improve reliability of the light emitting module 10 for the optical therapy by implementing the uniformity of the ultraviolet wavelength provided to the target region TA at 70% or more.

An embodiment may improve reliability of the light emitting module 10 for the optical therapy by implementing an ultraviolet wavelength having an effective wavelength (300 to 320 nm) for optical therapy of a high current drive of 200 mA or more.

An embodiment may provide a light emitting module and a medical equipment capable of improving reliability of a therapeutic ultraviolet wavelength having a full width at half maximum (FWHM) of 17 nm or less.

In an embodiment, the overall number of light emitting device packages 200 in a plurality of light emitting device packages 200 having a uniformity of light of 70% or more and a pitch of 30% to 50% of widths Y1 and X1 at the target region TA may be reduced, so that a size of the light emitting module 10 may be reduced, and thus manufacturing cost may be reduced.

Figure 18:
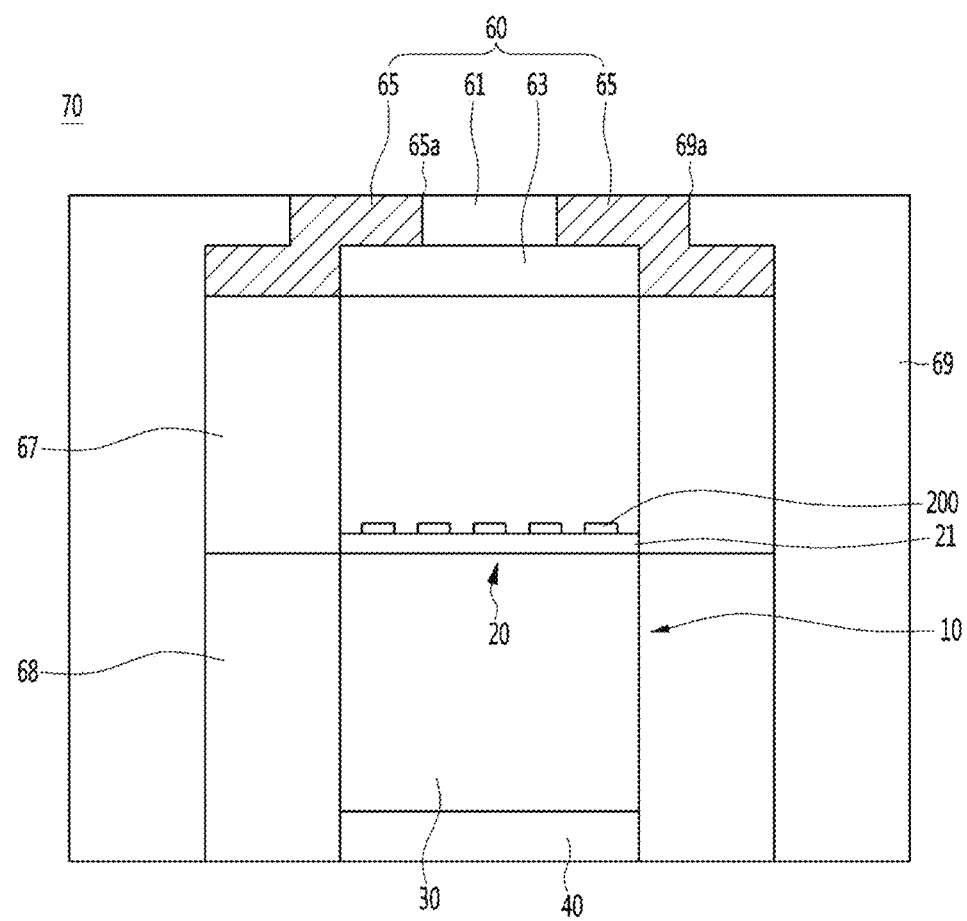
FIG. 18 is a cross-sectional view showing a medical equipment or a UV lamp including the light emitting module of FIG. 15.
Figure 19:
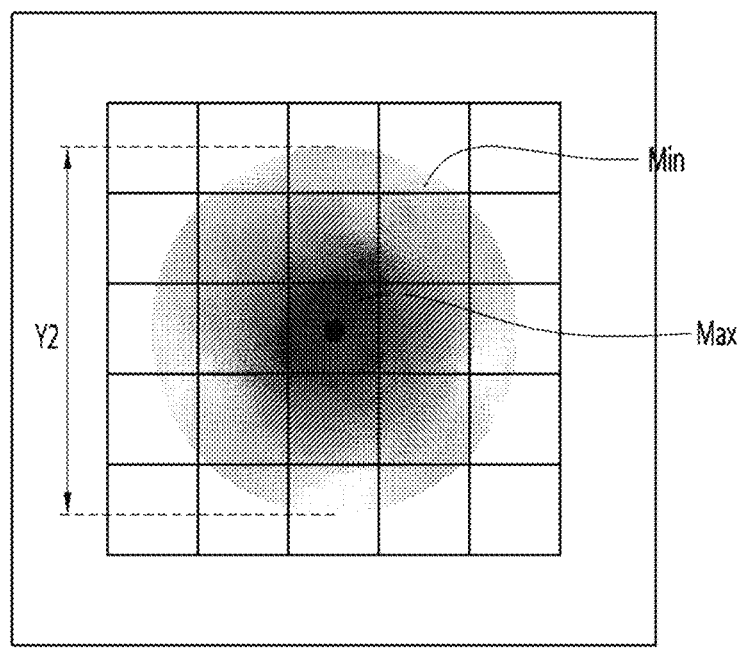
FIG. 19 is a diagram showing light uniformity of the light emitting module of FIG. 18.

FIG. 18 is a cross-sectional view showing a medical equipment having the light emitting module, as another embodiment, and FIG. 19 is a diagram showing light uniformity of the light emitting module of another embodiment.

As shown in FIGS. 16, 18, and 19, a medical equipment 70 including the light emitting module 10 may have a uniformity of 70% or more of light emitted from the light emitting unit 20 at a circular target region TA. Here, the minimum Min illumination of the edge region of the light emitting module of another embodiment is constant, so that another embodiment may have a higher uniformity than the light emitting module of an embodiment of FIGS. 16 to 17. Here, the minimum Min illumination of the light emitting module of an embodiment of FIG. 17 locally appears in an edge region of a rectangular target region. Therefore, the light emitting module of another embodiment may improve uniformity reliability of the target region TA. The configuration of the light emitting unit 20 and the first and second heat dissipation parts 30 and 40 of another embodiment may employ technical features of the light emitting module 20 of FIGS. 17 to 19.

The medical equipment 70 is a UV lamp, which requires a highly reliable light emitting module for medical treatment with a highly efficient UVB wavelength. In addition, in another embodiment, there is a need to implement the uniformity of the target region at 70% or more, and reduce the number of the light emitting device packages included in the light emitting module so as to reduce a size of the medical equipment 70 and reduce manufacturing costs. For this, an embodiment may have a high current drive of 200 mA or more and a full width at half maximum (FWHM) of 17 nm or less, and the light emitted from the light emitting unit 20 may have a uniformity of 70% or more at the circular target region TA. Here, the uniformity may be defined as minimum illumination (Min)/maximum illumination (Max) with respect to a center region where the illuminance is maximized and an edge region where the illuminance is minimized in the target region.

The medical equipment 70 may include an optical compensator 60. The optical compensator 60 may be disposed on the light emitting unit 20. The optical compensator 60 may be disposed at a light output region of the medical equipment 70. The optical compensator 60 may include first to third compensators 61, 63 and 65. The first compensator 61 may be disposed on the second compensator 63. The first compensator 61 may include a function of diffusing light. The first compensator 61 may include Teflon, but is not limited thereto. The first compensator 61 may be made of a material having high transmittance of light and excellent moisture-proof efficiency.

The second compensator 63 may be disposed under the first compensator 61 and may be disposed on the light emitting unit 20. The light emitted from the light emitting unit 20 may be directly irradiated to the second compensator 63. The second compensator 63 may include a material excellent in light transmittance. In addition, the second compensator 63 may include a function of diffusing light. For example, the second compensator 63 may include a glass material. The second compensator 63 may be formed of, for example, a transparent material such as LiF, $MgF_2$, $CaF_2$, $BaF_2$, $Al_2O_3$, $SiO_2$, or optical glass (N-BK7). The $SiO_2$ may be quad crystal or UV fused silica. Further, the second compensator 63 may be a low iron glass.

The third compensator 65 may include a function of surrounding and spreading outer edges of the first and second compensators 61 and 63. The third compensator 65 may include a function of diffusing light as a ring type. The first compensator 61 and the second compensator 63 may be disposed in an open region 65a of the third compensator 65. That is, the third compensator 65 may be coupled to circumferences of the first and second compensators 61 and 63. An area of the second compensator 63 or a width in a first direction may be wider than an area of the first compensator 61 or a width in a first direction.

In another embodiment, an optical compensator 60 including first to third compensators 61, 63, and 65 may disposed on the light emitting module to diffuse light emitted from the light emitting unit 20 to a target region TA, and thus uniformity may be improved.

The optical compensator 60 may be coupled to an upper open region 69a of a case 69, and at least a part thereof may be protruded. An inside of the case 69 may be provided with internal supports 67 and 68, and a lower support 68 for supporting an outside of the light emitting unit 20 and an upper support 67 for reflecting light from an upper portion may be included. The upper support 67 may be disposed under an outside of the third compensator 65 of the optical compensator 60, so that the third compensator 65 is in close contact with the case 69. Here, the top view of the light emitting unit 20 may have a circular shape, or a polygonal shape as shown in FIG. 16, and a shape of the inner holes of the inner supports 67 and 68 may differ according to such a shape.

The light emitting unit 20 includes a plurality of light emitting device packages 200. The plurality of light emitting device packages 200 may emit a UVB wavelength of 300 to 320 nm. The plurality of light emitting device packages 200 may have various wavelengths in 300 to 320 nm. The plurality of light emitting device packages 200 may selectively use various wavelengths for optical therapy and experiments. For this, the plurality of light emitting device packages 200 may have at least two different wavelengths. For example, a part of the light emitting device package 200 may emit a wavelength of 300 to 315 nm, and another part of the light emitting device package may emit a wavelength of 315 to 320 nm. The plurality of light emitting device packages 200 may emit a UVB wavelength of 300 to 320 nm which is driven by a high current of 100 mA or more. Specifically, the plurality of light emitting device packages 200 may implement an effective wavelength for optical therapy (300 to 320 nm) having a full width at half maximum (FWHM) of 17 nm or less. In general, an ultraviolet light emitting device having an FWHM of 20 nm or more destroys DNA, proteins and the like at 300 nm or less, particularly 298 nm or less, so that it is difficult to apply to medical equipment such as an Atopy treatment. The light emitting device package 200 of an embodiment may implement a full width at half maximum (FWHM) of 17 nm or less to improve reliability of the light emitting module 10 for optical therapy.

As shown in FIG. 19, the light emitting module of another embodiment may implement a uniformity of 70% or more in the circular target region TA in which the emitted light of ultraviolet wavelength is projected. The light uniformity may be defined as minimum illumination (Min)/maximum illumination (Max) with respect to a center region where the illuminance is maximized and an edge region where the illuminance is minimized in the circular target region TA. For example, the circular target region TA may be spaced apart from the light emitting unit 20 of the light emitting module 10 at 20 mm and have a diameter Y2 of 30 mm, but is not limited thereto. The circular target region TA may have a diameter Y2 of 10 to 40 mm. Specifically, the circular target region TA for an optical therapy may have a uniformity of 70% or more, which is defined as a minimum illumination (Min)/a maximum illumination (Max), and a minimum Min illumination of 10 $mW/cm^2$ or more.

When the uniformity is less than 70%, reliability of optical therapy may be deteriorated due to a difference in illumination between the center portion and the edge region of the circular target region TA.

Referring to FIG. 16, the plurality of light emitting device packages 200 may have a first pitch P1 in a first direction X-X' and may have a second pitch P2 in a second direction Y-Y' orthogonal to the first direction X-X'. The first and second pitches P1 and P2 may be 30 to 50% of the diameter Y2 of the circular target region TA. The first and second pitches P1 and P2 may be 10 mm or more. The first and second pitches P1 and P2 may be 10 to 15 mm. The first and second pitches P1 and P2 may be the same, but are not limited thereto. For example, the first and second pitches P1 and P2 may be different from each other. For example, an embodiment may include 25 light emitting device packages 200 having first and second pitches P1 and P2 of 10 mm in order to implement a uniformity of 70% or more in the circular target region TA spaced apart from the medical equipment 70 at 20 mm and having a diameter Y2 of 30 mm. Here, each of light emitting device packages 200 may have a luminous intensity Po of 10 mW or more.

Another embodiment may improve reliability of the medical equipment 70 for the optical therapy by implementing the uniformity of the ultraviolet wavelength provided at the target region TA at 70% or more.

Another embodiment may improve reliability of the medical equipment 70 for the optical therapy by implementing an ultraviolet wavelength having an effective wavelength (300 to 320 nm) for optical therapy of a high current drive of 200 mA or more.

Another embodiment may provide the medical equipment 70 capable of improving reliability of a therapeutic ultraviolet wavelength with a full width at half maximum (FWHM) of 17 nm or less.

In another embodiment, the overall number of light emitting device packages 200 in a plurality of light emitting device packages 200 having a uniformity of light of 70% or more and a pitch of 30% to 50% of the diameter Y2 at the circular target region TA may be reduced, so that a size of the light emitting module may be reduced, and thus manufacturing cost may be reduced. Therefore, another embodiment may reduce a size and a manufacturing cost of the medical equipment 70.

The light emitting device, the package, and the light emitting module having the same according to the embodiment may be applied to a medical equipment, a lighting unit, a indicating device, a lamp, a streetlight, a vehicle lighting device, a vehicle display device, a smart watch, and the like, but are not limited thereto.

The characteristics, structures and effects described in the embodiments above are included in at least one embodiment but are not limited to one embodiment. Furthermore, the characteristic, structure, and effect illustrated in each embodiment may be combined or modified for other embodiments by a person skilled in the art. Thus, it should be construed that contents related to such a combination and such a modification are included in the scope of the present invention.

Embodiments are mostly described above. However, they are only examples and do not limit the present invention. A person skilled in the art may appreciate that several variations and applications not presented above may be made without departing from the essential characteristic of embodiments. For example, each component specifically represented in the embodiments may be varied. In addition, it should be construed that differences related to such a variation and such an application are included in the scope of the present invention defined in the following claims.

INDUSTRIAL APPLICABILITY

The ultraviolet light emitting device according to the present invention may be used in various medical and therapeutic fields.

The UVB light emitting device according to the present invention may be used for medical equipment.

The light emitting device according to the present invention may be used for a biomedical optical therapy equipment.

The invention claimed is:
1. A light emitting device comprising:
an AlN template layer;
a first superlattice layer disposed on the AN template layer;
a second superlattice layer disposed on the first superlattice layer,
a first semiconductor layer disposed between the first and second superlattice layers;
a first conductive type semiconductor layer disposed on the second superlattice layer;
an active layer disposed on the first conductive type semiconductor layer and having a quantum well layer and a quantum wall layer;
an electron blocking layer disposed on the active layer; and
a second conductive type semiconductor layer disposed on the electron blocking layer,
wherein the first superlattice layer includes a first layer having an AlN semiconductor and a second layer having an AlGaN-based semiconductor,
the first semiconductor layer includes an AlGaN-based semiconductor,
the second superlattice layer includes a third layer having an AlGaN-based semiconductor and a fourth layer having an AlGaN-based semiconductor,
the first layer and the second layer are disposed alternately in the first superlattice layer,
the third layer and the fourth layer are disposed alternately in the second superlattice layer,
a composition of aluminum (Al) of each of the first semiconductor layer, the second layer and the third layer is equal to or greater than a composition of gallium (Ga),
wherein a difference between the composition of gallium and the composition of aluminum of each of the first semiconductor layer, the second layer and the third layer is 10% or less,
the first semiconductor layer has a thickness greater than a thickness of a single pair having the first layer and the second layer of the first superlattice layer, and
the active layer emits ultraviolet light,
wherein the composition of aluminum of the first semiconductor layer, the second layer and the third layer is 50% or more,
wherein the first semiconductor layer, the second layer and the third layer have a composition formula of $Al_xGa_{1-x}N$ ($0.5 \leq x \leq 0.6$), and the fourth layer has a composition formula of $Al_bGa_{1-b}N$ ($0.45 \leq b \leq 0.55$),
wherein the first conductive type semiconductor layer has a composition formula of $Al_xGa_{1-z}N$ ($0.45 \leq z \leq 0.55$),
the quantum well layer of the active layer is formed of an AlGaN-based semiconductor and the quantum wall layer is formed of an AlGaN-based semiconductor, and
the aluminum composition of the quantum wall layer is higher than that of the quantum well layer by 20% or more,
wherein the quantum well layer has a thickness of 25% or less of a thickness of the quantum wall layer, and
the active layer generates light of 295 nm to 315 nm,
wherein the electron blocking layer includes a plurality of barrier layers and a plurality of well layers,
the plurality of barrier layers include an AlGaN-based semiconductor,
the plurality of well layers include an AlGaN-based semiconductor,
each of the plurality of barrier layers has an aluminum composition higher than that of each of the plurality of well layers, each of the plurality of barrier layers has an aluminum composition higher than that of the quantum wall layer of the active layer, each of the plurality of well layers has an aluminum composition lower than that of the quantum wall layer of the active layer, and the plurality of barrier layers include a first barrier layer on the active layer and a second barrier layer under the second conductive type semiconductor layer, wherein the plurality of well layers are disposed between the first and second barrier layers, the plurality of barrier layers include a plurality of intermediate barrier layers disposed between the first and second barrier layers and the well layer, and an aluminum composition of each of the intermediate barrier layers is higher than that of the first and second barrier layers.

2. The light emitting device of claim 1, wherein the first barrier layer has a composition formula of $Al_pGa_{1-p}N$ ($0.50 \leq p \leq 0.74$), the second barrier layer has a composition formula of $Al_qGa_{1-q}N$ ($0.50 \leq q \leq 0.74$), and the intermediate barrier layer has a composition formula of $Al_rGa_{1-r}N$ ($0.55 \leq r \leq 0.74$).

3. The light emitting device of claim 1, wherein each of the first barrier layer, the second barrier layer, and the intermediate barrier layer is thicker than the well layer, and has a thickness of 3 nm to 10 nm, and a surface roughness of the second conductive type semiconductor layer is 1 nm or less.

4. The light emitting device of claim 1, wherein the plurality of well layers include a first well layer disposed between the first barrier layer and the intermediate barrier layer, a second well layer disposed between the intermediate barrier layers and a third well layer between the intermediate barrier layer and the second barrier layer, the first well layer has a composition formula of $Al_eGa_{1-e}N$ ($0.24 \leq e \leq 0.45$), the second well layer has a composition formula of $Al_fGa_{1-f}N$ ($0.24 \leq f \leq 0.48$), the third well layer has a composition formula of $Al_gGa_{1-g}N$ ($0.24 \leq g \leq 0.48$), the second conductive type semiconductor layer includes a first conductive semiconductor layer on the electron blocking layer and a second conductive semiconductor layer on the first conductive semiconductor layer, and the first conductive semiconductor layer has a composition formula of $Al_sGa_{1-s}N$ ($0.20 \leq s \leq 0.45$).

* * * * *